(12) United States Patent
Chen et al.

(10) Patent No.: US 7,563,324 B1
(45) Date of Patent: Jul. 21, 2009

(54) SYSTEM AND METHOD FOR COATING AN IMPLANTABLE MEDICAL DEVICE

(75) Inventors: Yung-Ming Chen, Cupertino, CA (US); Henjen Ho, San Jose, CA (US)

(73) Assignee: Advanced Cardiovascular Systems Inc., Santa Clara, CA (US)

(*) Notice: Subject to any disclaimer, the term of this patent is extended or adjusted under 35 U.S.C. 154(b) by 840 days.

(21) Appl. No.: 10/747,996

(22) Filed: Dec. 29, 2003

(51) Int. Cl.
*B05C 3/00* (2006.01)
(52) U.S. Cl. .................. 118/270; 118/264; 118/268; 118/269; 118/422; 118/429
(58) Field of Classification Search .............. 118/264, 118/268, 269, 500, 270, 271, 422, 429; 206/205, 206/207, 210, 212, 523; 427/2.1, 2.24, 429, 427/430.1; 623/1.45, 1.46
See application file for complete search history.

(56) References Cited

U.S. PATENT DOCUMENTS

| | | | |
|---|---|---|---|
| 2,072,303 A | 3/1937 | Herrmann et al. | |
| 2,386,454 A | 10/1945 | Frosch et al. | |
| 2,647,017 A | 7/1953 | Coulliette | |
| 2,701,559 A | 2/1955 | Cooper | |
| 3,288,728 A | 11/1966 | Gorham | |
| 3,687,135 A | 8/1972 | Stroganov et al. | |
| 3,773,737 A | 11/1973 | Goodman et al. | |
| 3,839,743 A | 10/1974 | Schwarcz | |
| 3,849,514 A | 11/1974 | Gray, Jr. et al. | |
| 3,900,632 A | 8/1975 | Robinson | |
| 4,075,045 A | 2/1978 | Rideout | |
| 4,104,410 A | 8/1978 | Malecki | |
| 4,110,497 A | 8/1978 | Hoel | |
| 4,132,357 A | 1/1979 | Blackinton | |
| 4,164,524 A | 8/1979 | Ward et al. | |
| 4,226,243 A | 10/1980 | Shalaby et al. | |
| 4,321,711 A | 3/1982 | Mano | |
| 4,323,071 A | 4/1982 | Simpson et al. | |
| 4,329,383 A | 5/1982 | Joh | 428/36 |
| 4,338,942 A | 7/1982 | Fogarty | |
| 4,343,931 A | 8/1982 | Barrows | |
| 4,346,028 A | 8/1982 | Griffith | |
| 4,439,185 A | 3/1984 | Lundquist | |
| 4,489,670 A | 12/1984 | Mosser et al. | |
| 4,516,972 A | 5/1985 | Samson et al. | |

(Continued)

FOREIGN PATENT DOCUMENTS

CA 2 008 312 7/1990

(Continued)

OTHER PUBLICATIONS

Anonymous, *Cardiologists Draw—Up The Dream Stent*, Clinica 710:15 (Jun. 17, 1996), http://www.dialogweb.com/cgi/document?reg=1061848202959, printed Aug. 25, 2003 (2 pages).

(Continued)

*Primary Examiner*—Laura Edwards
(74) *Attorney, Agent, or Firm*—Squire, Sanders & Dempsey L.L.P.

(57) ABSTRACT

A system and method for coating an implantable medical device, such as a stent, are provided.

25 Claims, 10 Drawing Sheets

U.S. PATENT DOCUMENTS

| | | | |
|---|---|---|---|
| 4,529,792 A | 7/1985 | Barrows | |
| 4,538,622 A | 9/1985 | Samson et al. | |
| 4,554,929 A | 11/1985 | Samson et al. | |
| 4,573,470 A | 3/1986 | Samson et al. | |
| 4,596,574 A | 6/1986 | Urist | |
| 4,599,085 A | 7/1986 | Riess et al. | |
| 4,608,984 A | 9/1986 | Fogarty | |
| 4,611,051 A | 9/1986 | Hayes et al. | |
| 4,612,009 A | 9/1986 | Drobnik et al. | |
| 4,616,593 A | 10/1986 | Kawamura et al. | |
| 4,616,652 A | 10/1986 | Simpson | |
| 4,629,563 A | 12/1986 | Wrasidlo | |
| 4,633,873 A | 1/1987 | Dumican et al. | |
| 4,638,805 A | 1/1987 | Powell | |
| 4,656,083 A | 4/1987 | Hoffman et al. | |
| 4,656,242 A | 4/1987 | Swan et al. | |
| 4,699,611 A | 10/1987 | Bowden | |
| 4,702,252 A | 10/1987 | Brooks et al. | |
| 4,718,907 A | 1/1988 | Karwoski et al. | |
| 4,722,335 A | 2/1988 | Vilasi | |
| 4,723,549 A | 2/1988 | Wholey et al. | |
| 4,732,152 A | 3/1988 | Wallstén et al. | |
| 4,733,665 A | 3/1988 | Palmaz | 128/343 |
| 4,739,762 A | 4/1988 | Palmaz | |
| 4,740,207 A | 4/1988 | Kreamer | |
| 4,743,252 A | 5/1988 | Martin, Jr. et al. | |
| 4,748,982 A | 6/1988 | Horzewski et al. | |
| 4,768,507 A | 9/1988 | Fischell et al. | |
| 4,774,039 A | 9/1988 | Wrasidlo | |
| 4,776,337 A | 10/1988 | Palmaz | |
| 4,800,882 A | 1/1989 | Gianturco | 128/343 |
| 4,816,339 A | 3/1989 | Tu et al. | |
| 4,818,559 A | 4/1989 | Hama et al. | |
| 4,828,561 A | 5/1989 | Woodroof | |
| 4,850,999 A | 7/1989 | Planck | |
| 4,865,870 A | 9/1989 | Hu et al. | |
| 4,871,542 A | 10/1989 | Vilhardt | |
| 4,877,030 A | 10/1989 | Beck et al. | |
| 4,878,906 A | 11/1989 | Lindemann et al. | |
| 4,879,135 A | 11/1989 | Greco et al. | |
| 4,880,683 A | 11/1989 | Stow | |
| 4,882,168 A | 11/1989 | Casey et al. | 424/468 |
| 4,886,062 A | 12/1989 | Wiktor | 128/343 |
| 4,902,289 A | 2/1990 | Yannas | |
| 4,906,423 A | 3/1990 | Frisch | |
| 4,931,287 A | 6/1990 | Bae et al. | |
| 4,932,353 A | 6/1990 | Kawata et al. | |
| 4,941,870 A | 7/1990 | Okada et al. | 600/36 |
| 4,943,346 A | 7/1990 | Mattelin | |
| 4,950,227 A | 8/1990 | Savin et al. | |
| 4,955,899 A | 9/1990 | Della Corna et al. | |
| 4,967,606 A | 11/1990 | Wells et al. | |
| 4,976,615 A * | 12/1990 | Kravitz | 433/75 |
| 4,977,901 A | 12/1990 | Ofstead | 128/772 |
| 4,988,356 A | 1/1991 | Crittenden et al. | |
| 4,994,033 A | 2/1991 | Shockey et al. | |
| 4,994,298 A | 2/1991 | Yasuda | |
| 4,994,560 A | 2/1991 | Kruper, Jr. et al. | |
| 5,015,505 A | 5/1991 | Cetnar | |
| 5,019,090 A | 5/1991 | Pinchuk | |
| 5,019,096 A | 5/1991 | Fox, Jr. et al. | |
| 5,028,597 A | 7/1991 | Kodama et al. | |
| 5,037,392 A | 8/1991 | Hillstead | |
| 5,037,427 A | 8/1991 | Harada et al. | |
| 5,040,548 A | 8/1991 | Yock | |
| 5,047,050 A | 9/1991 | Arpesani | |
| 5,049,132 A | 9/1991 | Shaffer et al. | |
| 5,053,048 A | 10/1991 | Pinchuk | |
| 5,059,166 A | 10/1991 | Fischell | |
| 5,059,169 A | 10/1991 | Zilber | |
| 5,059,211 A | 10/1991 | Stack et al. | |
| 5,062,829 A | 11/1991 | Pryor et al. | |
| 5,064,435 A | 11/1991 | Porter | |
| 5,078,720 A | 1/1992 | Burton et al. | |
| 5,081,394 A | 1/1992 | Morishita et al. | |
| 5,084,065 A | 1/1992 | Weldon et al. | |
| 5,085,629 A | 2/1992 | Goldberg et al. | |
| 5,087,244 A | 2/1992 | Wolinsky et al. | |
| 5,087,394 A | 2/1992 | Keith | |
| 5,100,429 A | 3/1992 | Sinofsky et al. | |
| 5,100,992 A | 3/1992 | Cohn et al. | |
| 5,102,402 A | 4/1992 | Dror et al. | |
| 5,104,410 A | 4/1992 | Chowdhary | |
| 5,108,416 A | 4/1992 | Ryan et al. | |
| 5,108,417 A | 4/1992 | Sawyer | |
| 5,108,755 A | 4/1992 | Daniels et al. | |
| 5,112,457 A | 5/1992 | Marchant | 204/165 |
| 5,116,318 A | 5/1992 | Hillstead | |
| 5,116,365 A | 5/1992 | Hillstead | |
| 5,123,917 A | 6/1992 | Lee | |
| 5,127,362 A | 7/1992 | Iwatsu et al. | |
| 5,133,742 A | 7/1992 | Pinchuk | |
| 5,134,192 A | 7/1992 | Feijen et al. | |
| 5,136,968 A * | 8/1992 | Sarada et al. | 118/264 |
| 5,147,370 A | 9/1992 | McNamara et al. | |
| 5,156,623 A | 10/1992 | Hakamatsuka et al. | |
| 5,156,911 A | 10/1992 | Stewart | |
| 5,158,548 A | 10/1992 | Lau et al. | |
| 5,163,951 A | 11/1992 | Pinchuk et al. | |
| 5,163,952 A | 11/1992 | Froix | |
| 5,163,958 A | 11/1992 | Pinchuk | |
| 5,165,919 A | 11/1992 | Sasaki et al. | 424/488 |
| 5,167,614 A | 12/1992 | Tessmann et al. | |
| 5,171,445 A | 12/1992 | Zepf | |
| 5,176,638 A | 1/1993 | Don Michael | |
| 5,188,734 A | 2/1993 | Zepf | |
| 5,192,311 A | 3/1993 | King et al. | |
| 5,197,977 A | 3/1993 | Hoffman, Jr. et al. | |
| 5,205,822 A | 4/1993 | Johnson et al. | |
| 5,213,561 A | 5/1993 | Weinstein et al. | |
| 5,213,576 A | 5/1993 | Abiuso et al. | |
| 5,219,980 A | 6/1993 | Swidler | |
| 5,222,971 A | 6/1993 | Willard et al. | |
| 5,225,750 A | 7/1993 | Higuchi et al. | |
| 5,226,889 A | 7/1993 | Sheiban | |
| 5,226,913 A | 7/1993 | Pinchuk | |
| 5,229,045 A | 7/1993 | Soldani | |
| 5,229,172 A | 7/1993 | Cahalan et al. | |
| 5,232,444 A | 8/1993 | Just et al. | |
| 5,234,456 A | 8/1993 | Silvestrini | |
| 5,234,457 A | 8/1993 | Andersen | |
| 5,236,447 A | 8/1993 | Kubo et al. | |
| 5,242,399 A | 9/1993 | Lau et al. | |
| 5,254,089 A | 10/1993 | Wang | |
| 5,254,091 A | 10/1993 | Aliahmad et al. | |
| 5,258,020 A | 11/1993 | Froix | |
| 5,258,419 A | 11/1993 | Rolando et al. | |
| 5,269,802 A | 12/1993 | Garber | |
| 5,272,012 A | 12/1993 | Opolski | 428/423.1 |
| 5,278,200 A | 1/1994 | Coury et al. | |
| 5,279,594 A | 1/1994 | Jackson | |
| 5,282,823 A | 2/1994 | Schwartz et al. | |
| 5,282,860 A | 2/1994 | Matsuno et al. | |
| 5,286,254 A | 2/1994 | Shapland et al. | |
| 5,289,831 A | 3/1994 | Bosley | |
| 5,290,271 A | 3/1994 | Jernberg | |
| 5,292,516 A | 3/1994 | Viegas et al. | 424/423 |
| 5,298,260 A | 3/1994 | Viegas et al. | 424/486 |
| 5,300,295 A | 4/1994 | Viegas et al. | 424/427 |
| 5,304,200 A | 4/1994 | Spaulding | |
| 5,306,250 A | 4/1994 | March et al. | |
| 5,306,286 A | 4/1994 | Stack et al. | |
| 5,306,294 A | 4/1994 | Winston et al. | |
| 5,306,501 A | 4/1994 | Viegas et al. | 424/423 |

| | | | | | | |
|---|---|---|---|---|---|---|
| 5,306,786 A | 4/1994 | Moens et al. | | 5,545,408 A | 8/1996 | Trigg et al. |
| 5,308,641 A | 5/1994 | Cahalan et al. | | 5,551,954 A | 9/1996 | Buscemi et al. |
| 5,314,472 A | 5/1994 | Fontaine | | 5,554,120 A | 9/1996 | Chen et al. |
| 5,318,531 A | 6/1994 | Leone | | 5,554,182 A | 9/1996 | Dinh et al. |
| 5,328,471 A | 7/1994 | Slepian ............ 604/101 | | 5,556,413 A | 9/1996 | Lam |
| 5,330,500 A | 7/1994 | Song | | 5,558,642 A | 9/1996 | Schweich, Jr. et al. |
| 5,330,768 A | 7/1994 | Park et al. ............ 424/501 | | 5,562,728 A | 10/1996 | Lazarus et al. |
| 5,336,518 A | 8/1994 | Narayanan et al. | | 5,569,463 A | 10/1996 | Helmus et al. ............ 424/426 |
| 5,342,283 A | 8/1994 | Good | | 5,571,135 A | 11/1996 | Fraser et al. |
| 5,342,348 A | 8/1994 | Kaplan | | 5,571,166 A | 11/1996 | Dinh et al. |
| 5,342,395 A | 8/1994 | Jarrett et al. | | 5,571,567 A | 11/1996 | Shah |
| 5,342,621 A | 8/1994 | Eury | | 5,578,046 A | 11/1996 | Liu et al. |
| 5,344,426 A | 9/1994 | Lau et al. | | 5,578,073 A | 11/1996 | Haimovich et al. ............ 623/1 |
| 5,344,455 A | 9/1994 | Keogh et al. | | 5,584,877 A | 12/1996 | Miyake et al. |
| 5,350,800 A | 9/1994 | Verhoeven et al. | | 5,588,962 A | 12/1996 | Nicholas et al. |
| 5,356,433 A | 10/1994 | Rowland et al. | | 5,591,199 A | 1/1997 | Porter et al. |
| 5,360,401 A | 11/1994 | Turnland et al. | | 5,591,224 A | 1/1997 | Schwartz et al. |
| 5,360,443 A | 11/1994 | Barone et al. | | 5,591,227 A | 1/1997 | Dinh et al. |
| 5,364,354 A | 11/1994 | Walker et al. | | 5,591,607 A | 1/1997 | Gryaznov et al. |
| 5,366,504 A | 11/1994 | Andersen et al. | | 5,593,403 A | 1/1997 | Buscemi |
| 5,368,560 A | 11/1994 | Rambo et al. | | 5,593,434 A | 1/1997 | Williams |
| 5,370,684 A | 12/1994 | Vallana et al. | | 5,595,722 A | 1/1997 | Grainger et al. |
| 5,380,299 A | 1/1995 | Fearnot et al. ............ 604/265 | | 5,599,301 A | 2/1997 | Jacobs et al. |
| 5,383,925 A | 1/1995 | Schmitt | | 5,599,307 A | 2/1997 | Bacher et al. |
| 5,383,927 A | 1/1995 | DeGoicoechea et al. | | 5,599,352 A | 2/1997 | Dinh et al. |
| 5,385,580 A | 1/1995 | Schmitt | | 5,599,922 A | 2/1997 | Gryaznov et al. |
| 5,387,450 A | 2/1995 | Stewart | | 5,605,696 A | 2/1997 | Eury et al. ............ 424/423 |
| 5,389,106 A | 2/1995 | Tower | | 5,607,442 A | 3/1997 | Fischell et al. |
| 5,399,666 A | 3/1995 | Ford | | 5,607,467 A | 3/1997 | Froix |
| 5,405,472 A | 4/1995 | Leone | | 5,609,629 A | 3/1997 | Fearnot et al. ............ 623/1 |
| 5,409,495 A | 4/1995 | Osborn | | 5,610,241 A | 3/1997 | Lee et al. |
| 5,411,466 A | 5/1995 | Hess | | 5,611,775 A | 3/1997 | Machold et al. |
| 5,411,477 A | 5/1995 | Saab | | 5,616,338 A | 4/1997 | Fox, Jr. et al. |
| 5,412,035 A | 5/1995 | Schmitt et al. | | 5,618,298 A | 4/1997 | Simon |
| 5,415,938 A | 5/1995 | Cahalan et al. | | 5,618,299 A | 4/1997 | Khosravi et al. |
| 5,417,981 A | 5/1995 | Endo et al. ............ 424/486 | | 5,620,420 A | 4/1997 | Kriesel |
| 5,423,849 A | 6/1995 | Engelson et al. | | 5,624,411 A | 4/1997 | Tuch ............ 604/265 |
| 5,423,885 A | 6/1995 | Williams | | 5,628,730 A | 5/1997 | Shapland et al. ............ 604/21 |
| 5,429,618 A | 7/1995 | Keogh | | 5,628,755 A | 5/1997 | Heller et al. |
| 5,441,515 A | 8/1995 | Khosravi et al. | | 5,628,781 A | 5/1997 | Williams et al. |
| 5,443,458 A | 8/1995 | Eury et al. | | 5,628,785 A | 5/1997 | Schwartz et al. |
| 5,443,496 A | 8/1995 | Schwartz et al. | | 5,628,786 A | 5/1997 | Banas et al. |
| 5,443,500 A | 8/1995 | Sigwart | | 5,629,077 A | 5/1997 | Turnlund et al. |
| 5,445,646 A | 8/1995 | Euteneuer et al. | | 5,631,135 A | 5/1997 | Gryaznov et al. |
| 5,447,724 A | 9/1995 | Helmus et al. ............ 424/426 | | 5,632,771 A | 5/1997 | Boatman et al. |
| 5,451,233 A | 9/1995 | Yock | | 5,632,840 A | 5/1997 | Campbell |
| 5,455,040 A | 10/1995 | Marchant ............ 424/426 | | 5,637,113 A | 6/1997 | Tartaglia et al. |
| 5,456,661 A | 10/1995 | Narciso, Jr. | | 5,644,020 A | 7/1997 | Timmermann et al. |
| 5,456,713 A | 10/1995 | Chuter | | 5,645,559 A | 7/1997 | Hachtman et al. |
| 5,458,615 A | 10/1995 | Klemm et al. | | 5,649,951 A | 7/1997 | Davidson |
| 5,460,610 A | 10/1995 | Don Michael | | 5,649,977 A | 7/1997 | Campbell ............ 623/1 |
| 5,462,990 A | 10/1995 | Hubbell et al. ............ 525/54.1 | | 5,653,691 A | 8/1997 | Rupp et al. |
| 5,464,450 A | 11/1995 | Buscemi et al. | | 5,656,080 A | 8/1997 | Staniforth et al. |
| 5,464,650 A | 11/1995 | Berg et al. ............ 427/2.3 | | 5,656,082 A | 8/1997 | Takatsuki et al. |
| 5,470,313 A | 11/1995 | Crocker et al. | | 5,658,995 A | 8/1997 | Kohn et al. ............ 525/432 |
| 5,470,603 A | 11/1995 | Staniforth et al. | | 5,667,523 A | 9/1997 | Bynon et al. |
| 5,476,476 A | 12/1995 | Hillstead | | 5,667,767 A | 9/1997 | Greff et al. ............ 424/9.411 |
| 5,476,509 A | 12/1995 | Keogh et al. | | 5,667,796 A | 9/1997 | Otten |
| 5,485,496 A | 1/1996 | Lee et al. | | 5,670,558 A | 9/1997 | Onishi et al. ............ 523/112 |
| 5,496,346 A | 3/1996 | Horzewski et al. | | 5,674,242 A | 10/1997 | Phan et al. |
| 5,500,013 A | 3/1996 | Buscemi et al. | | 5,679,400 A | 10/1997 | Tuch ............ 427/2.14 |
| 5,501,227 A | 3/1996 | Yock | | 5,693,085 A | 12/1997 | Buirge et al. |
| 5,502,158 A | 3/1996 | Sinclair et al. | | 5,693,376 A | 12/1997 | Fetherston et al. |
| 5,507,768 A | 4/1996 | Lau et al. | | 5,695,498 A | 12/1997 | Tower |
| 5,511,726 A | 4/1996 | Greenspan et al. | | 5,695,810 A | 12/1997 | Dubin et al. |
| 5,514,154 A | 5/1996 | Lau et al. | | 5,697,967 A | 12/1997 | Dinh et al. |
| 5,514,379 A | 5/1996 | Weissleder et al. | | 5,700,286 A | 12/1997 | Tartaglia et al. ............ 623/1 |
| 5,516,560 A | 5/1996 | Harayama et al. | | 5,702,754 A | 12/1997 | Zhong ............ 427/2.12 |
| 5,516,881 A | 5/1996 | Lee et al. | | 5,702,818 A | 12/1997 | Cahalan et al. |
| 5,527,337 A | 6/1996 | Stack et al. | | 5,707,385 A | 1/1998 | Williams |
| 5,537,729 A | 7/1996 | Kolobow | | 5,711,763 A | 1/1998 | Nonami et al. |
| 5,538,493 A | 7/1996 | Gerken et al. | | 5,711,812 A | 1/1998 | Chapek et al. |
| 5,545,209 A | 8/1996 | Roberts et al. | | 5,711,958 A | 1/1998 | Cohn et al. |

| Patent No. | Date | Inventor | Ref |
|---|---|---|---|
| 5,713,949 A | 2/1998 | Jayaraman | |
| 5,716,981 A | 2/1998 | Hunter et al. | 514/449 |
| 5,718,726 A | 2/1998 | Amon et al. | |
| 5,720,726 A | 2/1998 | Marcadis et al. | |
| 5,721,131 A | 2/1998 | Rudolph et al. | |
| 5,722,984 A | 3/1998 | Fischell et al. | |
| 5,723,219 A | 3/1998 | Kolluri et al. | |
| 5,725,549 A | 3/1998 | Lam | |
| 5,726,297 A | 3/1998 | Gryaznov et al. | |
| 5,728,068 A | 3/1998 | Leone et al. | |
| 5,728,751 A | 3/1998 | Patnaik | |
| 5,730,698 A | 3/1998 | Fischell et al. | |
| 5,733,326 A | 3/1998 | Tomonto et al. | |
| 5,733,327 A | 3/1998 | Igaki et al. | |
| 5,733,330 A | 3/1998 | Cox | |
| 5,733,564 A | 3/1998 | Lehtinen | |
| 5,733,925 A | 3/1998 | Kunz et al. | |
| 5,735,897 A | 4/1998 | Buirge | 623/12 |
| 5,741,554 A | 4/1998 | Tisone | |
| 5,741,881 A | 4/1998 | Patnaik | |
| 5,746,745 A | 5/1998 | Abele et al. | |
| 5,746,998 A | 5/1998 | Torchilin et al. | 424/9.4 |
| 5,756,457 A | 5/1998 | Wang et al. | |
| 5,756,476 A | 5/1998 | Epstein et al. | |
| 5,759,205 A | 6/1998 | Valentini | |
| 5,759,474 A | 6/1998 | Rupp et al. | |
| 5,765,682 A | 6/1998 | Bley et al. | |
| 5,766,204 A | 6/1998 | Porter et al. | |
| 5,766,239 A | 6/1998 | Cox | |
| 5,766,710 A | 6/1998 | Turnlund et al. | |
| 5,769,883 A | 6/1998 | Buscemi et al. | |
| 5,769,884 A | 6/1998 | Solovay | |
| 5,770,609 A | 6/1998 | Grainger et al. | |
| 5,772,864 A | 6/1998 | Møller et al. | |
| 5,776,184 A | 7/1998 | Tuch | 623/1 |
| 5,780,807 A | 7/1998 | Saunders | |
| 5,782,742 A | 7/1998 | Crocker et al. | |
| 5,783,657 A | 7/1998 | Pavlin et al. | |
| 5,788,626 A | 8/1998 | Thompson | |
| 5,788,979 A | 8/1998 | Alt et al. | 424/426 |
| 5,800,392 A | 9/1998 | Racchini | 604/96 |
| 5,800,516 A | 9/1998 | Fine et al. | |
| 5,804,318 A | 9/1998 | Pinchuk et al. | |
| 5,807,244 A | 9/1998 | Barot | |
| 5,810,871 A | 9/1998 | Tuckey et al. | |
| 5,810,873 A | 9/1998 | Morales | |
| 5,811,151 A | 9/1998 | Hendriks et al. | |
| 5,811,447 A | 9/1998 | Kunz et al. | |
| 5,820,917 A | 10/1998 | Tuch | 427/2.1 |
| 5,823,996 A | 10/1998 | Sparks | |
| 5,824,048 A | 10/1998 | Tuch | 623/1 |
| 5,824,049 A | 10/1998 | Ragheb et al. | 623/1 |
| 5,824,056 A | 10/1998 | Rosenberg | |
| 5,826,586 A | 10/1998 | Mishra et al. | |
| 5,830,178 A | 11/1998 | Jones et al. | 604/49 |
| 5,830,179 A | 11/1998 | Mikus et al. | |
| 5,830,217 A | 11/1998 | Ryan | |
| 5,830,461 A | 11/1998 | Billiar | |
| 5,830,879 A | 11/1998 | Isner | |
| 5,833,644 A | 11/1998 | Zadno-Azizi et al. | |
| 5,833,651 A | 11/1998 | Donovan et al. | |
| 5,833,659 A | 11/1998 | Kranys | |
| 5,834,582 A | 11/1998 | Sinclair et al. | |
| 5,836,962 A | 11/1998 | Gianotti | |
| 5,836,965 A | 11/1998 | Jendersee et al. | |
| 5,837,008 A | 11/1998 | Berg et al. | 623/1 |
| 5,837,313 A | 11/1998 | Ding et al. | 427/2.21 |
| 5,837,835 A | 11/1998 | Gryaznov et al. | |
| 5,840,009 A | 11/1998 | Fischell et al. | |
| 5,840,083 A | 11/1998 | Braach-Maksvytis | |
| 5,843,033 A | 12/1998 | Ropiak | |
| 5,843,119 A | 12/1998 | Shulewitz | |
| 5,843,172 A | 12/1998 | Yan | |
| 5,846,247 A | 12/1998 | Unsworth et al. | |
| 5,849,859 A | 12/1998 | Acemoglu | |
| 5,851,508 A | 12/1998 | Greff et al. | 424/9.411 |
| 5,853,408 A | 12/1998 | Muni | |
| 5,854,207 A | 12/1998 | Lee et al. | |
| 5,854,376 A | 12/1998 | Higashi | |
| 5,855,598 A | 1/1999 | Pinchuk | |
| 5,855,612 A | 1/1999 | Ohthuki et al. | |
| 5,855,618 A | 1/1999 | Patnaik et al. | |
| 5,857,998 A | 1/1999 | Barry | |
| 5,858,556 A | 1/1999 | Eckert et al. | |
| 5,858,746 A | 1/1999 | Hubbell et al. | 435/177 |
| 5,858,990 A | 1/1999 | Walsh | |
| 5,860,954 A | 1/1999 | Ropiak | |
| 5,865,814 A | 2/1999 | Tuch | 604/265 |
| 5,866,113 A | 2/1999 | Hendriks et al. | |
| 5,868,781 A | 2/1999 | Killion | |
| 5,869,127 A | 2/1999 | Zhong | 427/2.12 |
| 5,871,436 A | 2/1999 | Eury | |
| 5,871,437 A | 2/1999 | Alt | |
| 5,873,904 A | 2/1999 | Ragheb et al. | 623/1 |
| 5,874,101 A | 2/1999 | Zhong et al. | |
| 5,874,109 A | 2/1999 | Ducheyne et al. | |
| 5,874,165 A | 2/1999 | Drumheller | |
| 5,874,355 A | 2/1999 | Huang et al. | |
| 5,876,426 A | 3/1999 | Kume et al. | |
| 5,876,433 A | 3/1999 | Lunn | 623/1 |
| 5,876,743 A | 3/1999 | Ibsen et al. | |
| 5,877,224 A | 3/1999 | Brocchini et al. | 514/772.2 |
| 5,877,263 A | 3/1999 | Patnaik et al. | |
| 5,879,713 A | 3/1999 | Roth et al. | |
| 5,883,011 A | 3/1999 | Lin et al. | |
| 5,888,533 A | 3/1999 | Dunn | |
| 5,891,192 A | 4/1999 | Murayama et al. | |
| 5,893,840 A | 4/1999 | Hull et al. | |
| 5,893,852 A | 4/1999 | Morales | |
| 5,895,407 A | 4/1999 | Jayaraman | |
| 5,897,911 A | 4/1999 | Loeffler | |
| 5,897,955 A | 4/1999 | Drumheller | |
| 5,898,178 A | 4/1999 | Bunker | |
| 5,902,631 A | 5/1999 | Wang et al. | |
| 5,902,875 A | 5/1999 | Roby et al. | |
| 5,905,168 A | 5/1999 | Dos Santos et al. | |
| 5,906,759 A | 5/1999 | Richter | |
| 5,910,564 A | 6/1999 | Gruning et al. | |
| 5,914,182 A | 6/1999 | Drumheller | |
| 5,914,387 A | 6/1999 | Roby et al. | |
| 5,916,234 A | 6/1999 | Lam | |
| 5,916,870 A | 6/1999 | Lee et al. | |
| 5,919,893 A | 7/1999 | Roby et al. | |
| 5,921,416 A | 7/1999 | Uchara | |
| 5,922,005 A | 7/1999 | Richter et al. | |
| 5,922,393 A | 7/1999 | Jayaraman | |
| 5,925,552 A | 7/1999 | Keogh et al. | |
| 5,925,720 A | 7/1999 | Kataoka et al. | 525/523 |
| 5,928,916 A | 7/1999 | Keogh | |
| 5,932,299 A | 8/1999 | Katoot | |
| 5,935,135 A | 8/1999 | Bramfitt et al. | |
| 5,942,209 A | 8/1999 | Leavitt et al. | |
| 5,947,993 A | 9/1999 | Morales | |
| 5,948,018 A | 9/1999 | Dereume et al. | |
| 5,948,428 A | 9/1999 | Lee et al. | |
| 5,951,881 A | 9/1999 | Rogers et al. | |
| 5,954,744 A | 9/1999 | Phan et al. | |
| 5,955,509 A | 9/1999 | Webber et al. | 514/772.7 |
| 5,957,975 A | 9/1999 | Lafont et al. | |
| 5,958,385 A | 9/1999 | Tondeur et al. | |
| 5,962,138 A | 10/1999 | Kolluri et al. | |
| 5,965,720 A | 10/1999 | Gryaznov et al. | |
| 5,968,091 A | 10/1999 | Pinchuk et al. | |
| 5,968,092 A | 10/1999 | Buscemi et al. | |
| 5,969,422 A | 10/1999 | Ting et al. | |
| 5,971,954 A | 10/1999 | Conway et al. | 604/96 |

| Patent | Date | Inventor | Ref |
|---|---|---|---|
| 5,972,027 A | 10/1999 | Johnson | |
| 5,972,029 A | 10/1999 | Fuisz | |
| 5,972,505 A | 10/1999 | Phillips et al. | 428/397 |
| 5,976,155 A | 11/1999 | Foreman et al. | |
| 5,976,182 A | 11/1999 | Cox | |
| 5,980,564 A | 11/1999 | Stinson | |
| 5,980,928 A | 11/1999 | Terry | 424/427 |
| 5,980,972 A | 11/1999 | Ding | 427/2.24 |
| 5,981,568 A | 11/1999 | Kunz et al. | |
| 5,984,449 A | 11/1999 | Tajika et al. | |
| 5,986,169 A | 11/1999 | Gjunter | |
| 5,997,468 A | 12/1999 | Wolff et al. | |
| 5,997,517 A | 12/1999 | Whitbourne | 604/265 |
| 6,010,445 A | 1/2000 | Armini et al. | |
| 6,010,530 A | 1/2000 | Goicoechea | 623/1 |
| 6,010,573 A | 1/2000 | Bowlin | |
| 6,011,125 A | 1/2000 | Lohmeijer et al. | |
| 6,013,099 A | 1/2000 | Dinh et al. | |
| 6,015,541 A | 1/2000 | Greff et al. | 424/1.25 |
| 6,019,789 A | 2/2000 | Dinh et al. | |
| 6,024,918 A | 2/2000 | Hendriks et al. | |
| 6,027,510 A | 2/2000 | Alt | |
| 6,027,526 A | 2/2000 | Limon et al. | |
| 6,030,371 A | 2/2000 | Pursley | |
| 6,033,582 A | 3/2000 | Lee et al. | 216/37 |
| 6,033,719 A | 3/2000 | Keogh | |
| 6,034,204 A | 3/2000 | Mohr et al. | |
| 6,042,606 A | 3/2000 | Frantzen | |
| 6,042,875 A | 3/2000 | Ding et al. | 427/2.24 |
| 6,045,899 A | 4/2000 | Wang et al. | |
| 6,048,964 A | 4/2000 | Lee et al. | |
| 6,051,021 A | 4/2000 | Frid | |
| 6,051,576 A | 4/2000 | Ashton et al. | 514/255 |
| 6,051,648 A | 4/2000 | Rhee et al. | 525/54.1 |
| 6,054,553 A | 4/2000 | Groth et al. | |
| 6,056,906 A | 5/2000 | Werneth et al. | |
| 6,056,993 A | 5/2000 | Leidner et al. | 427/2.25 |
| 6,059,752 A | 5/2000 | Segal | |
| 6,059,810 A | 5/2000 | Brown et al. | |
| 6,060,451 A | 5/2000 | DiMaio et al. | 514/13 |
| 6,060,518 A | 5/2000 | Kabanov et al. | 514/781 |
| 6,063,092 A | 5/2000 | Shin | |
| 6,066,156 A | 5/2000 | Yan | |
| 6,071,266 A | 6/2000 | Kelley | |
| 6,071,305 A | 6/2000 | Brown et al. | |
| 6,074,659 A | 6/2000 | Kunz et al. | |
| 6,080,099 A | 6/2000 | Slater et al. | |
| 6,080,177 A | 6/2000 | Igaki et al. | |
| 6,080,190 A | 6/2000 | Schwartz | |
| 6,080,488 A | 6/2000 | Hostettler et al. | 428/423.3 |
| 6,083,258 A | 7/2000 | Yadav | |
| 6,086,610 A | 7/2000 | Duerig et al. | |
| 6,090,330 A | 7/2000 | Gawa et al. | |
| 6,093,199 A | 7/2000 | Brown et al. | |
| 6,093,463 A | 7/2000 | Thakrar | |
| 6,096,070 A | 8/2000 | Ragheb et al. | 623/1 |
| 6,096,525 A | 8/2000 | Patnaik | |
| 6,099,455 A | 8/2000 | Columbo et al. | |
| 6,099,559 A | 8/2000 | Nolting | |
| 6,099,561 A | 8/2000 | Alt | |
| 6,099,562 A | 8/2000 | Ding et al. | 623/1.46 |
| 6,103,230 A | 8/2000 | Billiar et al. | |
| 6,106,454 A | 8/2000 | Berg et al. | |
| 6,106,530 A | 8/2000 | Harada | |
| 6,106,889 A | 8/2000 | Beavers et al. | |
| 6,107,416 A | 8/2000 | Patnaik et al. | |
| 6,110,180 A | 8/2000 | Foreman et al. | |
| 6,110,188 A | 8/2000 | Narciso, Jr. | 606/153 |
| 6,110,483 A | 8/2000 | Whitbourne et al. | 424/423 |
| 6,113,629 A | 9/2000 | Ken | 623/1.1 |
| 6,117,479 A | 9/2000 | Hogan et al. | |
| 6,117,979 A | 9/2000 | Hendriks et al. | |
| 6,120,477 A | 9/2000 | Campbell et al. | |
| 6,120,491 A | 9/2000 | Kohn et al. | |
| 6,120,535 A | 9/2000 | McDonald et al. | |
| 6,120,536 A | 9/2000 | Ding et al. | 623/1.43 |
| 6,120,788 A | 9/2000 | Barrows | |
| 6,120,847 A | 9/2000 | Yang et al. | |
| 6,120,904 A | 9/2000 | Hostettler et al. | 428/423.3 |
| 6,121,027 A | 9/2000 | Clapper et al. | 435/180 |
| 6,123,712 A | 9/2000 | Di Caprio et al. | |
| 6,125,523 A | 10/2000 | Brown et al. | |
| 6,126,686 A | 10/2000 | Badylak et al. | |
| 6,127,173 A | 10/2000 | Eckstein et al. | |
| 6,129,761 A | 10/2000 | Hubbell | 623/11 |
| 6,129,928 A | 10/2000 | Sarangapani et al. | |
| 6,132,809 A | 10/2000 | Hynes et al. | |
| 6,136,333 A | 10/2000 | Cohn et al. | |
| 6,140,127 A | 10/2000 | Sprague | |
| 6,140,431 A | 10/2000 | Kinker et al. | |
| 6,143,354 A | 11/2000 | Koulik et al. | |
| 6,143,370 A | 11/2000 | Panagiotou et al. | |
| 6,149,574 A | 11/2000 | Trauthen et al. | |
| 6,150,630 A | 11/2000 | Perry et al. | |
| 6,153,252 A | 11/2000 | Hossainy et al. | 427/2.3 |
| 4,776,337 A | 12/2000 | Palmaz | |
| 6,156,373 A | 12/2000 | Zhong et al. | |
| 6,159,227 A | 12/2000 | Di Caprio et al. | |
| 6,159,229 A | 12/2000 | Jendersee et al. | |
| 6,159,951 A | 12/2000 | Karpeisky et al. | |
| 6,159,978 A | 12/2000 | Myers et al. | |
| 6,160,084 A | 12/2000 | Langer et al. | |
| 6,165,212 A | 12/2000 | Dereume et al. | 623/1.13 |
| 6,166,130 A | 12/2000 | Rhee et al. | |
| 6,168,617 B1 | 1/2001 | Blaeser et al. | |
| 6,168,619 B1 | 1/2001 | Dinh et al. | |
| 6,169,170 B1 | 1/2001 | Gryaznov et al. | |
| 6,171,609 B1 | 1/2001 | Kunz | |
| 6,172,167 B1 | 1/2001 | Stapert et al. | |
| 6,174,316 B1 | 1/2001 | Tuckey et al. | |
| 6,174,330 B1 | 1/2001 | Stinson | |
| 6,177,523 B1 | 1/2001 | Reich et al. | |
| 6,180,632 B1 | 1/2001 | Myers et al. | |
| 6,183,505 B1 | 2/2001 | Mohn, Jr. et al. | |
| 6,187,045 B1 | 2/2001 | Fehring et al. | |
| 6,193,727 B1 | 2/2001 | Foreman et al. | |
| 6,203,551 B1 | 3/2001 | Wu | 606/108 |
| 6,209,621 B1 | 4/2001 | Treacy | |
| 6,210,715 B1 | 4/2001 | Starling et al. | |
| 6,211,249 B1 | 4/2001 | Cohn et al. | |
| 6,214,115 B1 | 4/2001 | Taylor et al. | |
| 6,214,407 B1 | 4/2001 | Laube et al. | |
| 6,214,901 B1 | 4/2001 | Chudzik et al. | |
| 6,217,586 B1 | 4/2001 | Mackenzie | |
| 6,217,721 B1 | 4/2001 | Xu et al. | |
| 6,224,626 B1 | 5/2001 | Steinke | |
| 6,224,675 B1 | 5/2001 | Prentice et al. | |
| 6,224,894 B1 | 5/2001 | Jamiolkowski et al. | |
| 6,228,845 B1 | 5/2001 | Donovan et al. | |
| 6,231,590 B1 | 5/2001 | Slaikeu et al. | |
| 6,231,600 B1 | 5/2001 | Zhong | 623/1.42 |
| 6,240,616 B1 | 6/2001 | Yan | 29/527.2 |
| 6,242,041 B1 | 6/2001 | Katoot et al. | |
| 6,245,076 B1 | 6/2001 | Yan | |
| 6,245,099 B1 | 6/2001 | Edwin et al. | |
| 6,245,103 B1 | 6/2001 | Stinson | |
| 6,245,753 B1 | 6/2001 | Byun et al. | 514/56 |
| 6,245,760 B1 | 6/2001 | He et al. | |
| 6,248,129 B1 | 6/2001 | Froix | |
| 6,248,344 B1 | 6/2001 | Ylanen et al. | |
| 6,251,135 B1 | 6/2001 | Stinson et al. | |
| 6,251,136 B1 | 6/2001 | Guruwaiya et al. | 623/1.46 |
| 6,251,142 B1 | 6/2001 | Bernacca et al. | |
| 6,253,443 B1 | 7/2001 | Johnson | |
| 6,254,632 B1 | 7/2001 | Wu et al. | 623/1.15 |
| 6,258,099 B1 | 7/2001 | Mareiro et al. | |

| | | | | | |
|---|---|---|---|---|---|
| 6,258,121 B1 | 7/2001 | Yang et al. ............... 623/1.46 | 6,495,200 B1 | 12/2002 | Chan et al. |
| 6,258,371 B1 | 7/2001 | Koulik et al. | 6,503,538 B1 | 1/2003 | Chu et al. |
| 6,262,034 B1 | 7/2001 | Mathiowitz et al. | 6,503,556 B2 | 1/2003 | Harish et al. ............ 427/2.24 |
| 6,270,788 B1 | 8/2001 | Koulik et al. | 6,503,954 B1 | 1/2003 | Bhat et al. ............ 514/772.2 |
| 6,273,850 B1 | 8/2001 | Gambale | 6,504,307 B1 | 1/2003 | Malik et al. |
| 6,273,913 B1 | 8/2001 | Wright et al. | 6,506,437 B1 | 1/2003 | Harish et al. ............ 427/2.25 |
| 6,277,110 B1 | 8/2001 | Morales | 6,510,722 B1 | 1/2003 | Ching et al. |
| 6,277,449 B1 | 8/2001 | Kolluri et al. | 6,511,748 B1 | 1/2003 | Barrows |
| 6,279,368 B1 | 8/2001 | Escano et al. | 6,517,888 B1 | 2/2003 | Weber |
| 6,281,262 B1 | 8/2001 | Shikinami | 6,517,889 B1 | 2/2003 | Jayaraman |
| 6,283,947 B1 | 9/2001 | Mirzaee ................... 604/264 | 6,521,284 B1 | 2/2003 | Parsons et al. |
| 6,283,949 B1 | 9/2001 | Roorda ................ 604/288.02 | 6,524,232 B1 | 2/2003 | Tang et al. |
| 6,284,305 B1 | 9/2001 | Ding et al. ............... 427/2.28 | 6,524,347 B1 | 2/2003 | Myers et al. |
| 6,284,333 B1 | 9/2001 | Wang et al. | 6,527,801 B1 | 3/2003 | Dutta ..................... 623/1.46 |
| 6,287,332 B1 | 9/2001 | Bolz et al. | 6,527,863 B1 | 3/2003 | Pacetti et al. ............ 118/500 |
| 6,287,628 B1 | 9/2001 | Hossainy et al. .......... 427/2.3 | 6,528,526 B1 | 3/2003 | Myers et al. |
| 6,290,721 B1 | 9/2001 | Heath | 6,530,950 B1 | 3/2003 | Alvarado et al. |
| 6,293,966 B1 | 9/2001 | Frantzen | 6,530,951 B1 | 3/2003 | Bates et al. |
| 6,294,836 B1 | 9/2001 | Paranjpe et al. | 6,537,589 B1 | 3/2003 | Chae et al. |
| 6,296,603 B1 | 10/2001 | Turnlund et al. | 6,539,607 B1 | 4/2003 | Fehring et al. |
| 6,299,604 B1 | 10/2001 | Ragheb et al. ............ 604/265 | 6,540,776 B2 | 4/2003 | Sanders Millare et al. . 623/1.15 |
| 6,303,901 B1 | 10/2001 | Perry et al. | 6,540,777 B2 | 4/2003 | Stenzel |
| 6,306,176 B1 | 10/2001 | Whitbourne ............. 623/23.59 | 6,544,223 B1 | 4/2003 | Kokish ................ 604/103.01 |
| 6,312,459 B1 | 11/2001 | Huang et al. | 6,544,543 B1 | 4/2003 | Mandrusov et al. ......... 424/422 |
| 6,319,520 B1 | 11/2001 | Wuthrich et al. | 6,544,582 B1 | 4/2003 | Yoe ..................... 427/2.24 |
| 6,322,588 B1 | 11/2001 | Ogle et al. | 6,554,758 B2 | 4/2003 | Turnlund et al. |
| 6,322,847 B1 | 11/2001 | Zhong et al. | 6,554,854 B1 | 4/2003 | Flanagan |
| 6,327,772 B1 | 12/2001 | Zadno-Azizi et al. | 6,555,059 B1 | 4/2003 | Myrick et al. |
| 6,331,313 B1 | 12/2001 | Wong et al. ............... 424/427 | 6,555,157 B1 | 4/2003 | Hossainy ................ 427/2.24 |
| 4,733,665 C2 | 1/2002 | Palmaz | 6,558,733 B1 | 5/2003 | Hossainy et al. .......... 427/2.24 |
| 6,335,029 B1 | 1/2002 | Kamath et al. ............ 424/423 | 6,562,136 B1 | 5/2003 | Chappa et al. |
| 6,344,035 B1 | 2/2002 | Chudzik et al. | 6,565,599 B1 | 5/2003 | Hong et al. |
| 6,346,110 B2 | 2/2002 | Wu ......................... 606/108 | 6,565,659 B1 | 5/2003 | Pacetti et al. ............ 118/500 |
| 6,358,556 B1 | 3/2002 | Ding et al. ............... 427/2.24 | 6,569,191 B1 | 5/2003 | Hogan |
| 6,362,099 B1 | 3/2002 | Gandikota et al. | 6,569,193 B1 | 5/2003 | Cox et al. |
| 6,364,903 B2 | 4/2002 | Tseng et al. | 6,572,644 B1 | 6/2003 | Moein ..................... 623/1.11 |
| 6,375,458 B1 | 4/2002 | Moorleghem et al. | 6,572,672 B2 | 6/2003 | Yadav et al. |
| 6,375,826 B1 | 4/2002 | Wang et al. | 6,574,851 B1 | 6/2003 | Mirizzi |
| 6,379,379 B1 | 4/2002 | Wang | 6,582,417 B1 | 6/2003 | Ledesma et al. |
| 6,379,381 B1 | 4/2002 | Hossainy et al. .......... 623/1.42 | 6,585,755 B2 | 7/2003 | Jackson et al. |
| 6,387,118 B1 | 5/2002 | Hanson | 6,585,765 B1 | 7/2003 | Hossainy et al. .......... 623/1.45 |
| 6,387,121 B1 | 5/2002 | Alt | 6,585,926 B1 | 7/2003 | Mirzaee ................... 264/400 |
| 6,387,379 B1 | 5/2002 | Goldberg et al. | 6,592,614 B2 | 7/2003 | Lenker et al. |
| 6,388,043 B1 | 5/2002 | Langer et al. | 6,592,617 B2 | 7/2003 | Thompson |
| 6,395,325 B1 | 5/2002 | Hedge et al. | 6,596,296 B1 | 7/2003 | Nelson et al. |
| 6,395,326 B1 | 5/2002 | Castro et al. ............. 427/2.24 | 6,605,114 B1 | 8/2003 | Yan et al. |
| 6,406,738 B1 | 6/2002 | Hogan et al. | 6,605,154 B1 | 8/2003 | Villareal ................. 118/500 |
| 6,409,761 B1 | 6/2002 | Jang | 6,605,874 B2 | 8/2003 | Leu et al. |
| 6,413,272 B1 | 7/2002 | Igaki | 6,610,087 B1 | 8/2003 | Zarbatany et al. |
| 6,419,692 B1 | 7/2002 | Yang et al. ............... 623/1.15 | 6,613,072 B2 | 9/2003 | Lau et al. |
| 6,420,189 B1 | 7/2002 | Lopatin | 6,616,765 B1 | 9/2003 | Hossainy et al. |
| 6,423,092 B2 | 7/2002 | Datta et al. | 6,623,448 B2 | 9/2003 | Slater |
| 6,436,816 B1 | 8/2002 | Lee et al. | 6,625,486 B2 | 9/2003 | Lundkvist et al. |
| 6,444,567 B1 | 9/2002 | Besser et al. | 6,626,939 B1 | 9/2003 | Burnside et al. |
| 6,447,835 B1 | 9/2002 | Wang et al. | 6,635,269 B1 | 10/2003 | Jennissen |
| 6,451,373 B1 | 9/2002 | Hossainy et al. .......... 427/2.25 | 6,635,964 B2 | 10/2003 | Maex et al. |
| 6,454,738 B1 | 9/2002 | Tran et al. | 6,645,135 B1 | 11/2003 | Bhat |
| 6,455,424 B1 | 9/2002 | McTeer et al. | 6,645,195 B1 | 11/2003 | Bhat et al. |
| 6,461,632 B1 | 10/2002 | Gogolewski | 6,645,243 B2 | 11/2003 | Vallana et al. |
| 6,462,284 B1 | 10/2002 | Hashimoto | 6,645,547 B1 | 11/2003 | Shekalim et al. |
| 6,464,720 B2 | 10/2002 | Boatman et al. | 6,656,162 B2 | 12/2003 | Santini, Jr. et al. |
| 6,468,906 B1 | 10/2002 | Chan et al. | 6,656,216 B1 | 12/2003 | Hossainy et al. |
| 6,479,565 B1 | 11/2002 | Stanley | 6,656,506 B1 | 12/2003 | Wu et al. |
| 6,481,262 B2 | 11/2002 | Ching et al. | 6,660,034 B1 | 12/2003 | Mandrusov et al. |
| 6,482,834 B2 | 11/2002 | Spada et al. | 6,663,662 B2 | 12/2003 | Pacetti et al. |
| 6,485,512 B1 | 11/2002 | Cheng | 6,663,880 B1 | 12/2003 | Roorda et al. |
| 6,488,701 B1 | 12/2002 | Nolting et al. | 6,664,187 B1 | 12/2003 | Ngo et al. |
| 6,488,773 B1 | 12/2002 | Ehrhardt et al. | 6,664,335 B2 | 12/2003 | Krishnan |
| 6,491,666 B1 | 12/2002 | Santini, Jr. et al. | 6,666,214 B2 | 12/2003 | Canham |
| 6,492,615 B1 | 12/2002 | Flanagan | 6,666,880 B1 | 12/2003 | Chiu et al. |
| 6,494,862 B1 | 12/2002 | Ray et al. ............... 604/96.01 | 6,667,049 B2 | 12/2003 | Janas et al. |
| 6,494,908 B1 | 12/2002 | Huxel et al. | 6,669,723 B2 | 12/2003 | Killion et al. |
| 6,495,156 B2 | 12/2002 | Wenz et al. | 6,669,980 B2 | 12/2003 | Hansen |

| | | |
|---|---|---|
| 6,673,154 B1 | 1/2004 | Pacetti et al. |
| 6,673,385 B1 | 1/2004 | Ding et al. |
| 6,676,697 B1 | 1/2004 | Richter |
| 6,676,700 B1 | 1/2004 | Jacobs et al. |
| 6,679,980 B1 | 1/2004 | Andreacchi |
| 6,689,099 B2 | 2/2004 | Mirzaee |
| 6,689,375 B1 | 2/2004 | Wahlig et al. |
| 6,695,920 B1 | 2/2004 | Pacetti et al. |
| 6,703,307 B2 | 3/2004 | Lopatin et al. |
| 6,706,013 B1 | 3/2004 | Bhat et al. |
| 6,706,273 B1 | 3/2004 | Roessler |
| 6,709,379 B1 | 3/2004 | Brandau et al. |
| 6,709,514 B1 | 3/2004 | Hossainy |
| 6,712,845 B2 | 3/2004 | Hossainy |
| 6,713,119 B2 | 3/2004 | Hossainy et al. |
| 6,716,444 B1 | 4/2004 | Castro et al. |
| 6,719,934 B2 | 4/2004 | Stinson |
| 6,719,989 B1 | 4/2004 | Matsushima et al. |
| 6,720,402 B2 | 4/2004 | Langer et al. |
| 6,723,120 B2 | 4/2004 | Yan |
| 6,733,768 B2 | 5/2004 | Hossainy et al. |
| 6,739,033 B2 * | 5/2004 | Hijlkema et al. .............. 29/508 |
| 6,740,040 B1 | 5/2004 | Mandrusov et al. |
| 6,743,462 B1 | 6/2004 | Pacetti |
| 6,746,773 B2 | 6/2004 | Llanos et al. |
| 6,749,626 B1 | 6/2004 | Bhat et al. |
| 6,752,826 B2 | 6/2004 | Holloway et al. |
| 6,753,007 B2 | 6/2004 | Haggard et al. |
| 6,753,071 B1 | 6/2004 | Pacetti et al. |
| 6,758,859 B1 | 7/2004 | Dang et al. |
| 6,759,054 B2 | 7/2004 | Chen et al. |
| 6,764,505 B1 | 7/2004 | Hossainy et al. |
| 6,774,278 B1 | 8/2004 | Ragheb et al. |
| 6,776,792 B1 | 8/2004 | Yan et al. |
| 6,783,793 B1 | 8/2004 | Hossainy et al. |
| 6,818,063 B1 | 11/2004 | Kerrigan |
| 6,846,323 B2 | 1/2005 | Yip et al. |
| 6,860,946 B2 | 3/2005 | Hossainy et al. |
| 6,861,088 B2 | 3/2005 | Weber et al. |
| 6,865,810 B2 | 3/2005 | Stinson |
| 6,869,443 B2 | 3/2005 | Buscemi et al. |
| 6,878,160 B2 | 4/2005 | Gilligan et al. |
| 6,887,270 B2 | 5/2005 | Miller et al. |
| 6,887,485 B2 | 5/2005 | Fitzhugh et al. |
| 6,890,546 B2 | 5/2005 | Mollison et al. |
| 6,899,731 B2 | 5/2005 | Li et al. |
| 6,971,813 B2 * | 12/2005 | Shekalim et al. ............ 401/208 |
| 7,056,591 B1 | 6/2006 | Pacetti et al. |
| 7,198,675 B2 | 4/2007 | Fox et al. |
| 7,220,816 B2 | 5/2007 | Pacetti et al. |
| 7,258,891 B2 | 8/2007 | Pacetti |
| 7,323,210 B2 | 1/2008 | Castro et al. |
| 7,338,557 B1 | 3/2008 | Chen et al. |
| 2001/0007083 A1 | 7/2001 | Roorda |
| 2001/0014717 A1 | 8/2001 | Hossainy et al. |
| 2001/0016753 A1 | 8/2001 | Caprio et al. |
| 2001/0018469 A1 | 8/2001 | Chen et al. ................. 523/121 |
| 2001/0020011 A1 | 9/2001 | Mathiowitz et al. |
| 2001/0029351 A1 | 10/2001 | Falotico et al. |
| 2001/0037145 A1 | 11/2001 | Guruwaiya et al. ........ 623/1.15 |
| 2001/0044652 A1 | 11/2001 | Moore |
| 2001/0051608 A1 | 12/2001 | Mathiowitz et al. |
| 2002/0002399 A1 | 1/2002 | Huxel et al. |
| 2002/0004060 A1 | 1/2002 | Heublein et al. |
| 2002/0004101 A1 | 1/2002 | Ding et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0009604 A1 | 1/2002 | Zamora et al. |
| 2002/0016625 A1 | 2/2002 | Falotico et al. |
| 2002/0032414 A1 | 3/2002 | Ragheb et al. |
| 2002/0032434 A1 | 3/2002 | Chudzik et al. |
| 2002/0051730 A1 | 5/2002 | Bodnar et al. |
| 2002/0062148 A1 | 5/2002 | Hart |
| 2002/0065553 A1 | 5/2002 | Weber |
| 2002/0071822 A1 | 6/2002 | Uhrich |
| 2002/0077693 A1 | 6/2002 | Barclay et al. ............. 623/1.13 |
| 2002/0082679 A1 | 6/2002 | Sirhan et al. |
| 2002/0087123 A1 | 7/2002 | Hossainy et al. |
| 2002/0091433 A1 | 7/2002 | Ding et al. .................. 623/1.2 |
| 2002/0094440 A1 | 7/2002 | Llanos et al. |
| 2002/0111590 A1 | 8/2002 | Davila et al. |
| 2002/0116050 A1 | 8/2002 | Kocur |
| 2002/0120326 A1 | 8/2002 | Michal |
| 2002/0138133 A1 | 9/2002 | Lenz et al. |
| 2002/0142039 A1 | 10/2002 | Claude |
| 2002/0155212 A1 | 10/2002 | Hossainy ................... 427/2.25 |
| 2002/0161114 A1 | 10/2002 | Gunatillake et al. |
| 2002/0165608 A1 | 11/2002 | Llanos et al. |
| 2002/0176849 A1 | 11/2002 | Slepian |
| 2002/0183581 A1 | 12/2002 | Yoe et al. |
| 2002/0187632 A1 | 12/2002 | Marsh |
| 2002/0188037 A1 | 12/2002 | Chudzik et al. |
| 2002/0188277 A1 | 12/2002 | Roorda et al. |
| 2003/0003221 A1 | 1/2003 | Zhong et al. |
| 2003/0004141 A1 | 1/2003 | Brown |
| 2003/0028243 A1 | 2/2003 | Bates et al. |
| 2003/0028244 A1 | 2/2003 | Bates et al. |
| 2003/0031780 A1 | 2/2003 | Chudzik et al. |
| 2003/0032767 A1 | 2/2003 | Tada et al. |
| 2003/0033001 A1 | 2/2003 | Igaki |
| 2003/0036794 A1 | 2/2003 | Ragheb et al. |
| 2003/0039689 A1 | 2/2003 | Chen et al. |
| 2003/0040712 A1 | 2/2003 | Ray et al. |
| 2003/0040790 A1 | 2/2003 | Furst |
| 2003/0054090 A1 | 3/2003 | Hansen |
| 2003/0055482 A1 | 3/2003 | Schwager et al. |
| 2003/0059520 A1 | 3/2003 | Chen et al. |
| 2003/0060877 A1 | 3/2003 | Falotico et al. |
| 2003/0065377 A1 | 4/2003 | Davila et al. ................ 623/1.13 |
| 2003/0072868 A1 | 4/2003 | Harish et al. |
| 2003/0073961 A1 | 4/2003 | Happ |
| 2003/0083646 A1 | 5/2003 | Sirhan et al. |
| 2003/0083739 A1 | 5/2003 | Cafferata |
| 2003/0088307 A1 | 5/2003 | Shulze et al. |
| 2003/0093107 A1 | 5/2003 | Parsonage et al. |
| 2003/0097088 A1 | 5/2003 | Pacetti |
| 2003/0097173 A1 | 5/2003 | Dutta |
| 2003/0099712 A1 | 5/2003 | Jayaraman ................... 424/486 |
| 2003/0100865 A1 | 5/2003 | Santini, Jr. et al. |
| 2003/0105518 A1 | 6/2003 | Dutta |
| 2003/0105530 A1 | 6/2003 | Pirhonen |
| 2003/0113439 A1 | 6/2003 | Pacetti et al. |
| 2003/0113445 A1 | 6/2003 | Martin |
| 2003/0138487 A1 | 7/2003 | Hogan et al. |
| 2003/0150380 A1 | 8/2003 | Yoe |
| 2003/0157241 A1 | 8/2003 | Hossainy et al. |
| 2003/0158517 A1 | 8/2003 | Kokish |
| 2003/0171053 A1 | 9/2003 | Sanders |
| 2003/0185964 A1 | 10/2003 | Weber et al. |
| 2003/0187495 A1 | 10/2003 | Cully et al. |
| 2003/0190406 A1 | 10/2003 | Hossainy et al. |
| 2003/0196596 A1 * | 10/2003 | Nishi et al. .................. 118/300 |
| 2003/0203617 A1 | 10/2003 | Lane et al. |
| 2003/0207020 A1 | 11/2003 | Villareal |
| 2003/0208259 A1 | 11/2003 | Penhasi |
| 2003/0209835 A1 | 11/2003 | Chun et al. |
| 2003/0211230 A1 | 11/2003 | Pacetti et al. |
| 2003/0215564 A1 * | 11/2003 | Heller et al. ................ 427/2.25 |
| 2003/0226833 A1 | 12/2003 | Shapovalov et al. |
| 2003/0236565 A1 | 12/2003 | DiMatteo et al. |
| 2004/0018296 A1 | 1/2004 | Castro et al. |
| 2004/0029952 A1 | 2/2004 | Chen et al. |
| 2004/0047978 A1 | 3/2004 | Hossainy et al. |
| 2004/0047980 A1 | 3/2004 | Pacetti et al. |

| | | | | | | |
|---|---|---|---|---|---|---|
| 2004/0052858 A1 | 3/2004 | Wu et al. | | EP | 0 709 068 | 5/1996 |
| 2004/0052859 A1 | 3/2004 | Wu et al. | | EP | 0 716 836 | 6/1996 |
| 2004/0054104 A1 | 3/2004 | Pacetti | | EP | 0 732 087 | 9/1996 |
| 2004/0060508 A1 | 4/2004 | Pacetti et al. | | EP | 0 832 618 | 9/1996 |
| 2004/0062853 A1 | 4/2004 | Pacetti et al. | | EP | 0 756 853 | 2/1997 |
| 2004/0063805 A1 | 4/2004 | Pacetti et al. | | EP | 0 809 999 | 12/1997 |
| 2004/0071861 A1 | 4/2004 | Mandrusov et al. | | EP | 0 832 655 | 4/1998 |
| 2004/0072922 A1 | 4/2004 | Hossainy et al. | | EP | 0 834 293 | 4/1998 |
| 2004/0073298 A1 | 4/2004 | Hossainy | | EP | 0 850 604 | 7/1998 |
| 2004/0086542 A1 | 5/2004 | Hossainy et al. | | EP | 0 850 651 | 7/1998 |
| 2004/0086550 A1 | 5/2004 | Roorda et al. | | EP | 0 879 595 | 11/1998 |
| 2004/0093077 A1 | 5/2004 | White et al. | | EP | 0 910 584 | 4/1999 |
| 2004/0096504 A1 | 5/2004 | Michal | | EP | 0 923 953 | 6/1999 |
| 2004/0098095 A1 | 5/2004 | Burnside et al. | | EP | 0 953 320 | 11/1999 |
| 2004/0098117 A1 | 5/2004 | Hossainy et al. | | EP | 0 970 711 | 1/2000 |
| 2004/0111149 A1 | 6/2004 | Stinson | | EP | 0 972 498 | 1/2000 |
| 2004/0127970 A1 | 7/2004 | Saunders | | EP | 0 974 315 | 1/2000 |
| 2004/0143317 A1 | 7/2004 | Stinson et al. | | EP | 0 982 041 | 3/2000 |
| 2004/0167610 A1 | 8/2004 | Fleming, III | | EP | 1 023 879 | 8/2000 |
| 2004/0213893 A1 | 10/2004 | Boulais | | EP | 1 034 752 | 9/2000 |
| 2005/0038497 A1 | 2/2005 | Neuendorf et al. | | EP | 1 075 838 | 2/2001 |
| 2005/0043786 A1 | 2/2005 | Chu et al. | | EP | 1 103 234 | 5/2001 |
| 2005/0049694 A1 | 3/2005 | Neary | | EP | 1 192 957 | 4/2002 |
| 2005/0054774 A1 | 3/2005 | Kangas | | EP | 1 273 314 | 1/2003 |
| 2005/0055044 A1 | 3/2005 | Kangas | | EP | 0 869 847 | 3/2003 |
| 2005/0060020 A1 | 3/2005 | Jenson | | EP | 0 941 072 | 1/2004 |
| 2005/0064088 A1 | 3/2005 | Fredrickson | | FR | 2 753 907 | 4/1998 |
| 2005/0065501 A1 | 3/2005 | Wallace | | GB | 2 247 696 | 3/1992 |
| 2005/0065545 A1 | 3/2005 | Wallace | | GB | 2 316 086 | 1/2000 |
| 2005/0065593 A1 | 3/2005 | Chu et al. | | GB | 2 316 342 | 1/2000 |
| 2005/0074406 A1 | 4/2005 | Couvillon, Jr. et al. | | GB | 2 333 975 | 1/2000 |
| 2005/0074544 A1 | 4/2005 | Pacetti et al. | | GB | 2 336 551 | 1/2000 |
| 2005/0074545 A1 | 4/2005 | Thomas | | GB | 2 356 586 | 5/2001 |
| 2005/0079274 A1 | 4/2005 | Palasis et al. | | GB | 2 356 587 | 5/2001 |
| 2005/0137381 A1 | 6/2005 | Pacetti | | GB | 2 333 474 | 6/2001 |
| | | | | GB | 2 334 685 | 6/2001 |
| | FOREIGN PATENT DOCUMENTS | | | GB | 2 356 585 | 7/2001 |
| | | | | GB | 2 374 302 | 8/2001 |
| CA | 2 007 648 | 4/1991 | | GB | 2 370 243 | 6/2002 |
| CA | 1 322 628 | 10/1993 | | GB | 2 384 199 | 7/2003 |
| CA | 1 336 319 | 7/1995 | | JP | SHO49-48336 | 12/1974 |
| CA | 1 338 303 | 5/1996 | | JP | SHO54-18310 | 7/1979 |
| DE | 042 24 401 | 1/1994 | | JP | SHO60-28504 | 7/1985 |
| DE | 044 07 079 | 9/1994 | | JP | 21199867 | 5/1994 |
| DE | 197 31 021 | 1/1999 | | JP | HEI8-33718 | 2/1996 |
| DE | 199 16 086 | 10/1999 | | JP | HEI10-151190 | 6/1998 |
| DE | 198 56 983 | 12/1999 | | JP | 2919971 B2 | 7/1999 |
| EP | 0 108 171 | 5/1984 | | JP | 2001-190687 | 7/2001 |
| EP | 0 144 534 | 6/1985 | | SU | 0872531 | 10/1981 |
| EP | 0 301 856 | 2/1989 | | SU | 0876663 | 10/1981 |
| EP | 0 380 668 | 4/1989 | | SU | 0905228 | 2/1982 |
| EP | 0 351 314 | 1/1990 | | SU | 0790725 | 2/1983 |
| EP | 0 364 787 | 4/1990 | | SU | 1016314 | 5/1983 |
| EP | 0 396 429 | 11/1990 | | SU | 0811750 | 9/1983 |
| EP | 0 397 500 | 11/1990 | | SU | 1293518 | 2/1987 |
| EP | 0 464 755 | 1/1992 | | SU | 1477423 | 5/1989 |
| EP | 0 493 788 | 7/1992 | | WO | WO 89/03232 | 4/1989 |
| EP | 0 526 606 | 9/1992 | | WO | WO 90/01969 | 3/1990 |
| EP | 0 514 406 | 11/1992 | | WO | WO 90/04982 | 5/1990 |
| EP | 0 517 075 | 12/1992 | | WO | WO 90/06094 | 6/1990 |
| EP | 0 540 290 | 5/1993 | | WO | WO 91/11176 | 8/1991 |
| EP | 0 553 960 | 8/1993 | | WO | WO 91/12846 | 9/1991 |
| EP | 0 554 082 | 8/1993 | | WO | WO 91/17744 | 11/1991 |
| EP | 0 565 251 | 10/1993 | | WO | WO 91/17789 | 11/1991 |
| EP | 0 578 998 | 1/1994 | | WO | WO 92/10218 | 6/1992 |
| EP | 0 604 022 | 6/1994 | | WO | WO 93/06792 | 4/1993 |
| EP | 0 621 017 | 10/1994 | | WO | WO 94/09760 | 5/1994 |
| EP | 0 623 354 | 11/1994 | | WO | WO 94/21196 | 9/1994 |
| EP | 0 627 226 | 12/1994 | | WO | WO 95/10989 | 4/1995 |
| EP | 0 649 637 | 4/1995 | | WO | WO 95/11817 | 5/1995 |
| EP | 0 665 023 | 8/1995 | | WO | WO 95/24929 | 9/1995 |
| EP | 0 701 802 | 3/1996 | | WO | WO 95/29647 | 11/1995 |
| EP | 0 701 803 | 3/1996 | | WO | WO 95/33422 | 12/1995 |

| | | |
|---|---|---|
| WO | WO 96/28115 | 9/1996 |
| WO | WO 96/35516 | 11/1996 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/04415 | 2/1998 |
| WO | WO 98/07390 | 2/1998 |
| WO | WO 98/08463 | 3/1998 |
| WO | WO 98/17331 | 4/1998 |
| WO | WO 98/20863 | 5/1998 |
| WO | WO 98/23228 | 6/1998 |
| WO | WO 98/32398 | 7/1998 |
| WO | WO 98/36784 | 8/1998 |
| WO | WO 99/01118 | 1/1999 |
| WO | WO 99/03515 | 1/1999 |
| WO | WO 99/16386 | 4/1999 |
| WO | WO 99/38546 | 8/1999 |
| WO | WO 99/42147 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17459 | 3/2001 |
| WO | WO 01/17577 | 3/2001 |
| WO | WO 01/43727 | 6/2001 |
| WO | WO 01/45763 | 6/2001 |
| WO | WO 01/49338 | 7/2001 |
| WO | WO 01/51027 | 7/2001 |
| WO | WO 01/52772 | 7/2001 |
| WO | WO 01/57144 | 8/2001 |
| WO | WO 01/74414 | 10/2001 |
| WO | WO 01/91918 | 12/2001 |
| WO | WO 02/03890 | 1/2002 |
| WO | WO 02/26162 | 4/2002 |
| WO | WO 02/34311 | 5/2002 |
| WO | WO 02/47731 | 6/2002 |
| WO | WO 02/49771 | 6/2002 |
| WO | WO 02/056790 | 7/2002 |
| WO | WO 02/058753 | 8/2002 |
| WO | WO 02/087550 | 11/2002 |
| WO | WO 02/102283 | 12/2002 |
| WO | WO 03/000308 | 1/2003 |
| WO | WO 03/007918 | 1/2003 |
| WO | WO 03/007919 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/061841 | 7/2003 |
| WO | WO 03/072084 | 9/2003 |
| WO | WO 03/072086 | 9/2003 |
| WO | WO 03/080147 | 10/2003 |
| WO | WO 03/082368 | 10/2003 |
| WO | WO 2004/000383 | 12/2003 |
| WO | WO 2004/009145 | 1/2004 |
| WO | WO 2004/017947 | 3/2004 |
| WO | WO 2004/017976 | 3/2004 |
| WO | WO 2004/023985 | 3/2004 |
| WO | WO 2004/024339 | 3/2004 |

OTHER PUBLICATIONS

Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?req=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Capillary Action, http://www.ndt-ed.org/EducationResources/CommunityCollege/PenetrantTest/Introduction/Keywords/pt1.htm, 1 page, printed Aug. 13, 2003.

Capillary Force Lithography (CFL), Nano Precessing and Organic Devices Lab, 2 pages.

Capillary Rise of Liquid in Different Vanes Under Variable Residual Acceleration, http://www.zarm.uni-bremen.de/2forschung/grenzph/isoterm/cap_rise/kapst_en.htm, 2 pages, printed Jun. 24, 2003.

Chen et al., *The Kinetics of Wicking of Liquid Droplets into Yarns*, submitted to the Textile Research Journal, pp. 1-30.

Coating Techniques, Air Knife Coating, http://www.ferron-magnetic.co.uk/coatings/airknife.htm, 1 page, printed Jul. 1, 2003.

Coating Techniques, Gravure Coating, http://www.ferron-magnetic.co.uk/coatings/gravure.htm, 2 pages, printed Jul. 1, 2003.

Coating Techniques, Reverse Roll Coating, http://www.ferron-magnetic.co.uk/coatings/revroll.htm, 2 pages, printed Jul. 1, 2003.

Coating Techniques, Gap Coating, http://www.ferron-magnetic.co.uk/coatings/knife.htm, 1 page, printed Jul. 1, 2003.

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catherization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Dreyer et al., *Critical Velocities in Open Capillary Flows*, pp. 604-609.

Dutkiewicz, *Some Advances in Nonwoven Structures for Absorbency, Comfort and Aesthetics*, AUTEX Research Journal, vol. 2, No. 3, (Sep. 2002), pp. 153-165.

Eigler et al., *Local Arterial Wall Drug Delivery from a Polymer Coated Removable Metallic Stent: Kinetics, Distribution, and Bioactivity of Forskolin*, JACC, 4A(701-1), Abstract (Feb. 1994).

Erickson et al., *Numerical Simulations of Capillary-Driven Flows in Nonuniform Cross-Sectional Capillaries*, Journal of Colloid and Interface Science, vol. 250, pp. 422-430 (2002).

Fine Bubble Diffusers, Refraction Technologies Corp., 2 pages.

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Klocke et al, *How Soil Holds Water*, http://ianrpubs.unl.edu/fieldcrops/g964.htm, G90-964, 9 pages, printed Apr. 6, 2004.

Inoue et al., *An AB block copolymer of oligo(methyl methacrylate) and poly(acrylic acid) for micellar delivery of hydrophobic drugs*, Journal of Controlled Release 51:221-229 (1998).

Interfacial and Colloidal Phenomena Research Group, Illinois Institute of Technology, http://www.iit.edu/~wasan/exp1.html, 3 pages, printed Aug. 13, 2003.

Kataoka et al., *Block copolymer micelles as vehicles for drug delivery*, Journal of Controlled Release 24:119-132 (1993).

Konopoka, *In-Plane Moisture Transport in Nonwovens*, Nonwovens Cooperative Research Center, 56 pages.

Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).

Liquid Gravity Motor, http://www.drspark86.com/idea001.html, 2 pages, printed Jun. 24, 2003.

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials For Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Neimark et al., *Hierarchical Pore Structure and Wetting Properties of Single-Wall Carbon Nanotube Fibers*, Nano Letters, vol. 3, No. 3, pp. 419-423 (2003).

Nordrehaug et al., *A novel biocompatible coating applied to coronary stents*, European Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Porosimetry, Why characterize the porosity, 42 pages.

Refractron Technologies Corp., http://www.refractron.com/ecom/sp/cat=Custom+Applications, 1 page, printed Jun. 24, 2003.

Refractron Advanced Porous Ceramic Product Capabilities, http://www.refractron.com/ecom/sp/cat=Product+Information, 3 pages, printed Apr. 6, 2004.

Shigeno, *Prevention of Cerebrovascular Spasm By Bosentan, Novel Endothelin Receptor*, Chemical Abstract 125:212307 (1996).

Straube, Moisture, Materials, & Buildings, HPAC Engineering, pp. 2-7.

Surface Energy (Surface Wetting Capability), http://www.ndt-ed.org/EducationResources/CommunityCollege/PenetrantTest/PTMaterials/surfaceenergy.htm, 3 pages, printed Apr. 6, 2004.

Taher et al., *Capillary Interaction Between a Small Thin Solid Plate and a Liquid*, 4 pages.

Van Beusekom et al., *Coronary stent coatings*, Coronary Artery Disease 5(7):590-596 (Jul. 1994).

Vapor-Jet Capillary Pump—How it Works, Vapor Inc., http://www.vapore.com/tech_howto.htm, 2 pages, printed Aug. 13, 2003.

Viscosity, slides, 7 pages.

The Wicking Well System, http://www.decorative.com/wicking.html, 1 page, printed Jun. 24, 2003.

The 14th International Young Physicists Tournament, The winning report, Mgr. Martin Plesch, Research Center for Quantum Information, Slovak Academy of Sciences, Dubravska cesta 9, Bratislava, Slovakia, 5 pages.

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

Zhmud et al., *Dynamics of Capillary Rise*, Journal of Colloid and Interface Science, vol. 228, pp. 263-269 (2000).

Angioplasty.org., *Balloons and Stents*, http://www.ptca.org/devices04.html, printed Oct. 15, 2004, 2 pages.

Anonymous, *Typical Parylene Properties*, 3 pages (no date).

Ansari, *End-to-End Tubal Anastomosis Using an Absorbable Stent*, Fertility and Sterility, vol. 32, No. 2, pp. 197-201 (Aug. 1979).

Ansari, *Tubal Reanastomosis Using Absorbable Stent*, International Journal of Fertility, vol. 23, No. 4, pp. 242-243 (1978).

Beach et al., *Xylylene Polymers*, Encyclopedia of Polymer Science and Engineering, vol. 17, 2nd Edition, pp. 990-1025 (1989).

Boston Scientific, *Express $^{2TM}$ Coronary Stent System*, http://www.bostonscientific.com/med_specialty/deviceDetail.jsp?task=tskBasicDevice.jsp&sectionId=4&relId=2,74,75,76&deviceId=11001&uniqueId=MPDB1180&clickType=endeca, printed Aug. 8, 2005, 1 page.

Bull, *Parylene Coating for Medical Applications*, Medical Product Manufacturing News, 2 pages (Mar. 1993).

Casper et al., *Fiber-Reinforced Absorbable Composite for Orthopedic Surgery*, Polymeric Materials Science and Engineering, vol. 53, pp. 497-501(1985).

Charlson et al., *Temperature Selective Deposition of Parylene-C*, IEEE Transactions of Biomedical Engineering, vol. 39, No. 2, pp. 202-206 (Feb. 1992).

Crowe et al., *Absorption and Intestinal Metabolism of SDZ-RAD and Rapamycin in Rats*, Drug Metabolism and Disposition, vol. 27, No. 5, pp. 627-632 (1999).

De Scheerder et al., *Biocompatibility of polymer-coated oversized metallic stents implanted in normal porcine coronary arteries*, Atherosclerosis, vol. 114, pp. 105-114 (1995).

Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9, No. 2, pp. 111-130 (Mar./Apr. 1996).

Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9, No. 6, pp. 495-504 (Nov./Dec. 1996).

Detweiler et al., *Sutureless Anastomosis of the Small Intestine and the Colon in Pigs Using an Absorbable Intraluminal Stent and Fibrin Glue*, Journal of Investigative Surgery, vol. 8, No. 2, pp. 129-140 (Mar. 1995).

Detweiler et al., *Sutureless Cholecystojejunostomy in Pigs Using an Absorbable Intraluminal Stent and Fibrin Glue*, Journal of Investigative Surgery, vol. 9, No. 1, pp. 13-26 (Jan./Feb. 1996).

Devanathan et al., *Polymeric Conformal Coatings for Implantable Electronic Devices*, IEEE Transactions on Biomedical Engineering, vol. BME-27, No. 11, pp. 671-675 (1980).

Duerig et al., *A comparison of balloon-and self-expanding stents*, Min. Invas. Ther. & Allied Technol., vol. 11, No. 4, pp. 173-178 (2002).

EFD, *780S Series Spray Valves Valvemate™ 7040 Controller Operating Manual*, 24 pages (2002).

Elbert et al., *Conjugate Addition Reactions Combined with Free-Radical Cross-Linking for the Design of Materials for Tissue Engineering*, Biomacromolecules, vol. 2, pp. 430-441 (2001).

Eskin et al., *Growth of Cultured Calf Aortic Smooth Muscle Cells on Cardiovascular Prosthetic Materials*, J. Biomed. Mater. Res. vol. 10, pp. 113-122 (1976).

Eskin et al., *Tissue Cultured Cells: Potential Blood Compatible Linings for Cardiovascular Prostheses*, Polymer Science and Technology, vol. 14, pp. 143-161 (no date).

Fischell et al., *Low-Dose, β -Particle Emission from 'Stent' Wire Results in Complete, Localized Inhibition of Smooth Muscle Cell Proliferation*, Circulation, vol. 90, No. 6, pp. 2956-2963 (Dec. 1994).

Fischell et al., *The Bx Velocity™ Stent*, 5 pages, Biocompatibles Ltd. (2001).

Gengenbach et al., *Evolution of the Surface Composition and Topography of Perflurinated Polymers Following Ammonia-Plasma Treatment*, Plasma Surface Modifications of Polymers, pp. 123-146 (1994).

Gercken et al., *Results of the Jostent Coronary Stent Graft Implantation in Various Clinical Settings: Procedural and Follow-Up Results*, vol. 56, No. 3, pp. 353-360 (2002).

Gölander et al., *RF-Plasma-Modified Polystyrene Surfaces for Studying Complement Activation*, J. Biomater. Sci. Plymer Edn., vol. 4, No. 1 pp. 25-30 (1992)

Guidant, *ACS RX Multi-Link™ Coronary Stent System*, 6 pages (no date).

Guidant, *Guidant Multi-Link Vision OTW Coronary Stent System*, 2 pages (no date).

Hahn et al., *Biocompatibility of Glow-Discharge-Polmerized Films and Vacuum-Deposited Parylene*, Journal of Applied Polymer Science: Applied Polymer Symposium 38, 55-64 (1984).
Hahn et al., *Glow Discharge Polymers as Coatings for Implanted Devices*, John M. Dalton Research Center, University of Missouri-Columbia and the Graduate Center for Materials Research, pp. 109-113 (1981).
He et al., *Assessment of Tissue Blood Flow Following Small Artery Welding with an Intraluminal Dissolvable Stent*, Microsurgery, vol. 19, No. 3, pp. 148-152 (1999).
Hehrlein et al., *Low-Dose Radioactive Endovascular Stents Prevent Smooth Muscle Cell Proliferation and Neointimal Hyperplasia in Rabbits*, Circulation, vol. 92, No. 6, pp. 1570-1575 (Sep. 15, 1995).
Hollahan et al., *Attachment of Amino Groups to Polymer Surfaces by Radiofrequency Plasmas*, Journal of Applied Polymer Science, vol. 13, pp. 807-816 (1969).
Huang et al., *Biodegradable Polymers Derived from Aminoacids*, Macromol. Symp. 144, 7-32 (1999).
Impulse Jetting, *About Us*, http://www.impulsejetting.com/about.html, printed Dec. 18, 2000, 1 page.
Impulse Jetting, *Our Technology*, http://www.impulsejetting.com/tech1.html, printed Dec. 18, 2000, 1 page.
Inagaki et al., *Hydrophilic Surface Modification of Polyethylene by No-Plasma Treatment*, Adhesion Sci. Technol., vol. 4, No. 2, pp. 99-107 (1990).
Itabashi et al., *Electroless Deposited CoWB for Copper Diffusion Barrier Metal*, International Interconnect Technology Conference, pp. 285-287 (2002).
John Ritchie Production Group, *Production of Stents* (presentation), 15 pages (Apr. 24, 2003).
Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, vol. 37, 391-407 (1999).
Kawai et al., *Physiologically Based Pharmacokinetics of Cyclosporine A: Extension to Tissue Distribution Kinetics in Rats and Scale-up to Human*, The Journal of Pharmacology and Experimental Therapeutics, vol. 287, No. 2, pp. 457-468 (1998).
Kelley et al., *Totally Resorbable High-Strength Composite Material*, Advances in Biomedical Polymers, vol. 35, pp. 75-85 (1987).
Kovarik et al., *Pharmacokinetic and Pharmacodynamic Assessments of HMG-CoA Reductase Inhibitors When Coadministered with Everolimus*, Journal of Clinical Pharmacology, vol. 42, pp. 222-228 (2002).
Kubies et al., *Microdomain Structure In polylactide-block-poly(ethylene oxide) copolymer films*, Biomaterials, vol. 21, pp. 529-536 (2000).
Kutryk et al., *Coronary Stenting: Current Perspectives, a companion to the Handbook of Coronary Stents*, 16 pages (1999).
Lambert et al., *Localized Arterial Wall Drug Delivery From a Polymer-Coated Removable Metallic Stent*, Circulation, vol. 90, No. 2, pp. 1003-1011 (Aug. 1994).
Lemos et al., *Coronary Restenosis After Sirolimus-Eluting Stent Implantation*, Circulation, vol. 108, No. 3, pp. 257-260 (Jul. 22, 2003).
Liermann et al., *Prophylactic Endovascular Radiotherapy to Prevent Intimal Hyperplasia after Stent Implantation in Femoropopliteal Arteries*, CardioVascular and Interventional Radiology, vol. 17, pp. 12-16 (1994).
Loeb et al., *Parylene as a Chronically Stable, Reproducible Microelectrode Insulator*, IEEE Transactions on Biomedical Engineering, pp. 121-128 (Mar. 1977).
Loh et al., *Plasma Enhanced Parylene Deposition*, Antec, pp. 1099-1103 (1991).
Machine Solutions, *FFS700 MSI Balloon Form/Fold/Set Equipment (PTCA), FFS800 MSI Balloon Form/Fold/Set Equipment (PTA)*, http://machinesolutions.org/ffs7_8.html, printed Nov. 21, 2003 (2 pgs.).
Machine Solutions, *SC700 MSI Stent Crimping Equipment (PTCA), SC800 MSI Stent Crimping Equipment (PTA)*, http://www.machinesolutions.org/sc7_8.html, printed Nov. 21, 2003, 2 pages.

Malik et al., *Development of an Energetic Ion Assisted Mixing and Deposition Process for $TIN_x$ and Diamondlike Carbon Films, Using a Co-axial Geometry in Plasma Source Ion Implantation*, J. Vac. Sci. Technol. A, vol. 15, No. 6, pp. 2875-2879 (Nov./Dec. 1997).
Malik et al., *Overview of plasma source ion implantation research at University of Wisconsin-Madison*, J. Vac. Sci. Technol. B, No. 12, vol. 2, pp. 843-849 (Mar./Apr. 1994).
Malik et al., *Sheath dynamics and dose analysis for planar targets in plasma source ion implantation*, Plasma Sources Sci. Technol. Vol. 2, pp. 81-85 (1993).
Mauduit et al., *Hydrolytic degradation of films prepared from blends of high and low molecular weight poly(DL-lactic acid)s*, J. Biomed. Mater. Res., vol. 30, pp. 201-207 (1996).
Middleton et al., *Synthetic biodegradable polymers as orthopedic devices*, Biomaterials, vol. 21, pp. 2335-2346 (2000).
Moody, *Vacuum Coating Ultrasonic Transducers*, 1 page, Sensors (Dec. 1993).
Muller et al., *Advances in Coronary Angioplasty: Endovascular Stents*, Coronary Artery Disease, vol. 1, No. 4, pp. 438-448 (Jul./Aug. 1990).
Nichols et al., *Electrical Insulation of Implantable Devices by Composite Polymer Coatings*, ISA Transactions, vol. 26, No. 4, pp. 15-18 (1987).
Nova Tran™ Custom Coating Services, *Parylene Conformal Coating*, 8 pages (no date).
Olson, *Parylene, a Biostabel Coating for Medical Applications*, Specialty Coating Systems, Inc. Nova Tran™ Parylene Coating Services (no date).
Para Tech Coating Company, *Galxyl, Parylene Coatings by Para Tech*, 1 page (no date).
Para Tech Coating Company, *Lab Top® Parylene Deposition System*, 2 pages (no date).
Peuster et al., *A novel approach to temporary stenting: degradable cardiovascular stents produced from corrodible metal-results 6-18 months after implantation into New Zealand white rabbits*, Heart vol. 86, pp. 563-569 (2001).
Pietrzak et al., *Bioabsorbable Fixation Devices: Status for the Craniomaxillofacial Surgeon*, Journal of Craniofacial Surgery, vol. 8, No. 2, pp. 92-96 (1997).
Pietrzak et al., *Bioresorbable Implants—Practical Considerations*, Bone, vol. 19, No. 1, Supplement, pp. 109S-119S (Jul. 1996).
Poncin-Epaillard et al., *Reactivity of a Polypropylene Surface Modified in a Nitrogen Plasma*, Plasma Surface Modification of Polymers pp. 167-180 (1994).
Redman, *Clinical Experience with Vasovasostomy Utilizing Absorbable Intravasal Stent*, Urology, vol. XX, No. 11, pp. 59-61 (Jul. 1982).
Rust et al., *The Effect of Absorbable Stenting on Postoperative Stenosis of the Surgically Enlarged Maxillary Sinus Ostia in a Rabbit Animal Model*, Archives of Otolaryngology, Head and Neck Surgery, vol. 122, pp. 1395-1397 (Dec. 1996).
Sadhir et al., *The Adhesion of Glow-Discharge Polymers, Silastic and Parylene to Implantable Platinum Electrodes: Results of Tensil Pull tests After Exposure to Isotonic Sodium Chloride*, Biomaterials, vol. 2, pp. 239-243 (Oct. 1981).
Saotome, et al., *Novel Enzymatically Degradable Polymers Comprising α-Amino Acid, 1,2-Ethanediol, and Adipic Acid*, Chemistry Letters, pp. 21-24, (1991).
Schatz, *A View of Vascular Stents*, Circulation, vol. 79, No. 2, pp. 445-457 (Feb. 1989).
Scheuer et al., *Model of plasma source ion implantation in planar, cylindrical, and spherical geometries*, J. Appl. Phys., vol. 67, No. 3, pp. 1241-1245 (Feb. 1990).
Schmidt et al., *Long-term Implants of Parylene-C Coated Microelectrodes*, Medical & Biological Engineering & Computing, pp. 96-101 (Jan. 1988).
Serkova et al., *Tissue Distribution and Clinical Monitoring of the Novel Macrolide Immunosuppressant SDZ-RAD and its Metabolites in Monkey Lung Transplant Recipients: Interaction with Cyclosporine*, The Journal of Pharmacology and Experimental Therapeutics, vol. 294, No. 1, pp. 323-332 (2000).
Serruys et al., *I Like the Candy, I Hate the Wrapper; the $^{32}P$ Radioactive Stent*, Circulation, vol. 101, pp. 3-7 (Jan. 2000).

Shamim et al., *Measurement of electron emission due to energetic ion bombardment in plasma source ion implantation*, J. Appl. Phys., vol. 70, No. 9, pp. 4756-4759 (Nov. 1991).

Shamim et al., *Measurements of Spatial and Temporal Sheath Evolution for Spherical and Cylindrical Geometries in Plasma Source Ion Implantation*, J. Appl. Phys., vol. 69, No. 5, pp. 2904-2908 (Mar. 1991).

Sono Tek Corporation, *AccuMist™ for Single Stent Coating Applications*, http://www.sono-tek.com/biomedical/accumist_stent.html, printed Aug. 2, 2005, 3 pages.

Sono Tek Corporation, *MediCoat™ DES 1000, Benchtop Stent Coating System*, http://www.sono-tek.com/biomedical/medicoat_standalone.html, printed Aug. 2, 2005, 4 pages.

Sono Tek Corporation, *MicroMist for Stent Coating*, http://www.sono-tek.com/biomedical/micromist_stent.html, printed Aug. 2, 2005, 3 pages.

Specialty Coating Systems, Inc., *The Parylene Press*, 4 pages (Summer 1993).

Specialty Coating Systems, Inc., *The Parylene Press*, 6 pages (Spring 1993).

Specialty Coating Systems, Inc., *The Parylene Press*, 7 pages (Winter 1992).

Specialty Coating Systems, *Parylene and Nova Tran™ Parylene Coating Services, for Unmatched Conformal Coating Performance*, 21 pages (no date).

Specialty Coating Systems, *Parylene, a Biostable Coating for Medical Applications*, 6 pages (no date).

Specialty Coating Systems, *Repair and Recoating of Parylene Coated Printed Circuit Boards*, 15 pages (no date).

Tamai et al., *Initial and 6-Month Results of Biodegradable Poly-l-Lactic Acid Coronary Stents in Humans*, Circulation, vol. 102, pp. 399-404 (2000).

Trident, Inc., http://www.tridentintl.com/subbody.html, printed Dec. 18, 2000, 1 page.

Trident, Inc., *Product Lines*, http://www.tridentintl.com/products-apps/ultrajet.html, printed Dec. 18, 2000, 3 pages.

Tsuji et al., *Biodegradable Polymeric Stents*, Current Interventional Cardiology Reports vol. 3, pp. 10-17 (2001).

Union Carbide Adhesion Promoters, *Union Carbide A-174 Silane*, 5 pages (Jan. 1968).

Union Carbide Electronics Division, *Parylene Environmentally Compatible Conformal Coatings for Electronic Components Assemblies and Precision Parts*, 14 pages (no date).

Union Carbide, *Abrasion Resistance of Parylene and Other Conformal Circuit Board Coatings*, Parylene Products, No. 4, 13 pages (Oct. 1977).

Union Carbide, *Adhesion Promotion Systems for Parylene*, Parylene Products, No. 15, Revision 1, 8 pages (Oct. 1977).

Union Carbide, *Adhesion Promotion Systems for Parylene*, Technology Letter, No. 15, 13 pages (Oct. 1975).

Union Carbide, *Evaluation of Parylene and Other Pellicles as Beam Splitters*, Parylene Products, No. 8, Edited, 19 pages (Oct. 1977).

Union Carbide, *Fluorescent Parylene Coatings*, Parylene Products, No. 7 Revision 1, 8 pages (Oct. 1977).

Union Carbide, *Fluorescent Parylene Coatings*, Technology Letter, No. 7, 8 pages (Oct. 1973).

Union Carbide, *Mechanical Protection Criteria for Thin Conformal Coatings*, Parylene Products, No. 3, 21 pages (Oct. 1977).

Union Carbide, *Method for Repair and Patching of Parylene Coated Printed Circuit Boards*, Parylene Products, No. 2 Revision 1, 9 pages (Oct. 1977).

Union Carbide, *Microencapsulation by Vapor Deposition*, Parylene Products, No. 6, 12 pages (Oct. 1977).

Union Carbide, *MIL I 46058, Qualification of Parylene N, C, and D*, Parylene Products, No. 1 Revision 2, 8 pages (Oct. 1977).

Union Carbide, *Parylene Bibliography*, Parylene Products, No. 5, Revision 4, 17 pages (Jan. 18, 1982).

Union Carbide, *Parylene Conformal Coatings for Hybrid Microelectronics*, Parylene Products, No. 9, 23 pages (Oct. 1973).

Union Carbide, *Parylene Pellicles for Space Applications*, Parylene Products, No. 10, 50 pages (Oct. 1977).

Union Carbide, *Parylene Pyrolysis Kinetics*, Parylene Products, No. 11, 12 pages (Oct. 1977).

Union Carbide, *Parylene Pyrolysis Kinetics*, Technology Letter, No. 11, 12 pages (May 1974).

Union Carbide, *Parylene Removal with Oxygen Plasmas*, Parylene Products, No. 18, 7 pages (Aug. 1977).

Union Carbide, *Printed Circuit Board Masking Techniques for Use with Parylene*, No. 14, Revision 1, 11 pages (Oct. 1977).

Union Carbide, *Solvent Resistance of the Parylenes*, Parylene Products, No. 12, Revision 1, 5 pages (Oct. 1977).

Union Carbide, *The Selective Removal of Parylene by Plasma Etching*, No. 13, Revision 1, 7 pages (Oct. 1977).

Union Carbide, *Thermal Endurance of the Parylenes in Air*, Parylene Products, No. 16, 4 pages (Mar. 1976).

Union Carbide, *Vapor Phase Adhesion Promotion Systems*, Parylene Products, No. 17, Revision 1, 11 pages (Oct. 1977).

van der Giessen et al., *"Edge Effect" of $^{32}P$ Radioactive Stents is Caused by the Combination of Chronic Stent Injury and Radioactive Dose Falloff*, Circulation, vol. 104, pp. 2236-2241 (Oct. 30, 2001).

von Recum et al., *Degradation of polydispersed poly(L-lactic acid) to modulate lactic acid release*, Biomaterials, vol. 16, pp. 441-445 (1995).

Wiesendanger et al., *Contributions of Scanning Probe Microscopy and Spectroscopy to the Investigation and Fabrication of Nanometer-Scale Structures*, J. Vac. Sci. Technol. B, vol. 12, No. 2, pp. 515-529 (Mar./Apr. 1994).

Wong et al., *An Update on Coronary Stents*, Cardio, 8 pages (Feb. 1992).

World Precision Instruments, Inc., http://www.wpiinc.com/WPI_Web/Pumps/pneumatic_Fig.gif, printed Sep. 30, 2002, 1 page.

World Precision Instruments, Inc., *Nanoliter Injector*, http://www.wpiinc.com/WPI_Web/Microinjection/Nanoliter_Injector.html, printed Jun. 10, 2005, 3 pages.

World Precision Instruments, Inc., *Nanoliter Injector*, http://www.wpi-europe.com/products/microinjection/nanoliter.htm printed Jun. 10, 2005, 2 pages.

World Precision Instruments, Inc., *Pneumatic PicoPumps*, http://www.wpieurope.com/products/microinjection/picopumps.htm, printed Jun. 10, 2005, 4 pages.

World Precision Instruments, Inc., *Pneumatic PicoPumps*, http://www.wpiinc.com/WPI_Web/Microinjection/Pneumatic_PicoPumps.html, printed Jun. 10, 2005, 4 pages.

Yau et al., *Modern Size-Exclusion Liquid Chromatography*, Wiley-Interscience Publication, 9 pages (1979).

Yuen et al., *Tissue response to potential neuroprosthetic materials implanted subdurally*, Biomaterials, vol. 8, pp. 57-62 (Mar. 1987).

Zimarino et al., *Analysis of Stent Edge Restenosis with Different Forms of Brachytherapy*, The American Journal of Cardiology, vol. 89, pp. 322-325 (Feb. 1, 2002).

Zylberman et al., *Comparative Study of Electroless Co(W,P) and Co(Mo,P) Thin -Films for Capping and Barrier Layers for Cu Metallization*, 2002 Advanced Metallization Conference, 2 pages (no date).

U.S. Appl. No. 10/255,913, filed Sep. 26, 2002, Tang et al.

U.S. Appl. No. 10/304,669, filed Nov. 25, 2002, Madriaga et al.

U.S. Appl. No. 10/317,435, filed Dec. 11, 2002, Hossainy et al.

\* cited by examiner

FIG. 7A  FIG. 7B

SYSTEM AND METHOD FOR COATING AN IMPLANTABLE MEDICAL DEVICE

BACKGROUND OF THE INVENTION

1. Field of the Invention

This invention relates to a system for coating an implantable medical device, such as a stent, and a method of coating a device using the system.

2. Description of the Background

Blood vessel occlusions are commonly treated by mechanically enhancing blood flow in the affected vessels, such as by employing a tubular implantable medical device known as a stent. Stents act as scaffoldings, functioning to physically hold open and, if desired, to expand the wall of the passageway. Stents are capable of being compressed, so that they can be inserted through small lumens via catheters, and then expanded to a larger diameter once they are at the desired location.

FIG. 1 illustrates a conventional stent 10 formed from a plurality of structural elements including struts 12 and connecting elements 14. The plurality of struts 12 are radially expandable and interconnected by connecting elements 14 that are disposed between adjacent struts 12, leaving lateral openings or gaps 16 between adjacent struts 12. Struts 12 and connecting elements 14 define a tubular stent body having an outer, tissue-contacting surface and an inner surface.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that can produce adverse or even toxic side effects for the patient.

One method of medicating a stent involves the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent surfaces a coating of the polymer and the therapeutic substance impregnated in the polymer.

As noted above, one of the methods of applying a drug composition to a stent involves spraying the composition onto the stent. The composition can be atomized to produce small droplets. Atomization is used because the droplet size can be made smaller than the size of the stent's structural elements, thus enabling a substantially conformal coating. However, there are potential shortcomings associated with a spray coating process. For instance, many of the drugs and polymers that are applied to stents are toxic when inhaled by humans. As the polymeric drug solutions are atomized, therefore, great care must be taken to avoid occupational exposure to the personnel conducting the process. Hoods, glove boxes, enclosures, and shrouds can be used to prevent toxic aerosol inhalation, but at a cost of decreased efficiency and increased expenditures on equipment. In light of these safety and manufacturing concerns, a stent coating method that avoids atomization of the coating can be advantageous.

Another disadvantage of a spray coating process is that the transfer efficiency can be comparatively low. Only droplets which fall onto the stent's structural elements are incorporated into the coating. If the spray pattern is larger than the stent, much of the spray can be wasted. Moreover, the stent's body can have a number of open spaces or gaps between the structural elements that allow the spray to pass through, and therefore be unused. The components of the coating compositions can be very expensive. For instance, many of the drugs applied to stents are small molecule agents or biologically derived substances such as peptides and gene therapy agents that are very costly. A stent coating method which transfers the coating solution in a more direct manner to the stent structure would therefore have a manufacturing cost advantage.

The dipping or spraying of the composition onto the stent can result in a complete coverage of all stent surfaces, i.e., both luminal (inner) and abluminal (outer) surfaces, with a coating. However, from a therapeutic standpoint, drugs need only be released from the abluminal stent surface, and possibly the sidewalls. Moreover, having a coating on the luminal surface of the stent can have a detrimental impact on the stent's deliverability as well as the coating's mechanical integrity. A polymeric coating can increase the coefficient of friction between the stent and the delivery balloon. Additionally, some polymers have a "sticky" or "tacky" consistency. If the polymeric material either increases the coefficient of friction or adherers to the catheter balloon, the effective release of the stent from the balloon after deflation can be compromised. Adhesive, polymeric stent coatings can also experience extensive balloon sheer damage post-deployment, which could result in a thrombogenic luminal stent surface. Accordingly, there is a need to eliminate or minimize the amount of coating that is applied to the inner surface of the stent. Reducing or eliminating the polymer from the stent luminal surface also means a reduction in total polymer load, which is a desirable goal for optimizing long-term biocompatibility of the device.

A method for preventing the composition from being applied to the inner surface of the stent is by placing the stent over a mandrel that fittingly mates within the inner diameter of the stent. A tubing can be inserted within the stent such that the outer surface of the tubing is in contact with the inner surface of the stent. A tubular mandrel that makes contact with the inner surface of the stent can cause coating defects in spraying and dipping application processes. A high degree of surface contact between the stent and the support apparatus can provide regions in which the sprayed or dipped liquid composition can flow, wick, and collect. As the solvent evaporates, the excess composition hardens to form excess coating at and around the contact points between the stent and the support apparatus. Upon the removal of the coated stent from the mandrel, the excess coating may stick to the mandrel, thereby removing some of the coating from the stent in the form of peels as shown in FIG. 2, or leaving bare areas as shown in FIG. 3. Alternatively, as illustrated in FIG. 4, the excess coating may stick to the stent, thereby leaving excess coating as clumps or pools on the struts or webbing between the struts. These types of defects can cause adverse biological responses after the coated stent is implanted into a biological lumen.

Accordingly, the present invention provides a system and method for coating an implantable medical device that addresses these concerns and others needs as are apparent to one having ordinary skill in the art.

SUMMARY OF THE INVENTION

In accordance with one aspect of the invention a system for coating an implantable medical device with a coating composition is provided, including a reservoir holding a coating composition, an applicator including a coating surface and a porous region in fluid communication with the coating composition in the reservoir, wherein the porous region is capable of conveying the coating composition from the reservoir to the coating surface, and a support element to support an implantable medical device in close proximity to or in contact with the coating surface of the applicator. In one embodiment, the applicator includes a tubular body. In another embodiment, the coating surface comprises a flat substrate on which the device can be placed. In yet another embodiment, the applicator is made from a ceramic or polymeric material.

In accordance with another aspect of the present invention, an applicator for coating an implantable medical device with a coating composition is provided, comprising a hollow tubular body having a bore configured to receive an implantable medical device; and a plurality of fibers disposed along the bore of the body, the fibers configured to receive a coating composition to apply the coating composition to the implantable medical device.

In accordance with a further aspect, a system for coating an implantable medical device with a coating composition is provided, including a reservoir holding a coating composition, and an applicator including a coating surface and a porous region in communication with the coating composition in the reservoir, wherein the porous region is capable of loading the coating surface with the coating composition from the reservoir by capillary action. In one embodiment, the system further comprises a support element to support an implantable medical device in close proximity to or in contact with the coating surface.

In accordance with yet another aspect, a method of coating an implantable medical device is provided, including positioning a part of an applicator in a reservoir having a coating composition, the applicator including a coating surface and a porous region capable of conveying the coating composition from the reservoir to the coating surface, allowing the coating composition to be conveyed to the coating surface, and transferring at least some of the coating composition from the coating surface onto an implantable medical device.

In accordance with another aspect of the invention, a method of coating an implantable medical device is provided, including exposing a portion of an applicator to a coating composition, the applicator including a coating surface, allowing a layer of the coating composition to be formed on the coating surface of the applicator by capillary action, and transferring at least some of the coating composition from the coating surface onto an implantable medical device.

BRIEF DESCRIPTION OF THE FIGURES

FIGS. 7A, 7B and 7C are top views of a coating surface of an applicator in accordance with different embodiments;

FIGS. 10A, 10B, 11, 12A, 12B, 13A, 13B, 14A, 14B, 14C and 14D illustrate coating systems for coating a stent in accordance with various other embodiments of the present invention.

DETAILED DESCRIPTION

Implantable Medical Device

Figure 1:
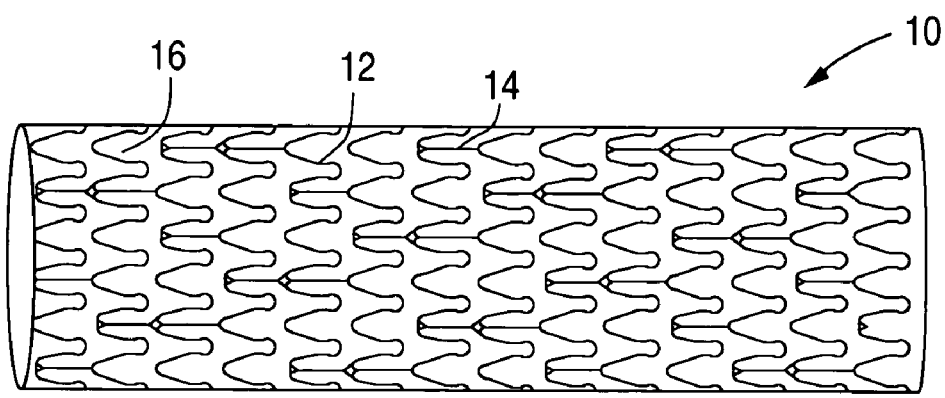
FIG. 1 illustrates a conventional stent.

Herein is disclosed a method and system for coating an implantable medical device. The implantable medical device can be a tubular device, such as a stent. In the interests of brevity, a method and system for coating a stent including a polymeric coating are described herein. However, one of ordinary skill in the art will understand that other medical devices having therapeutic capabilities can be coated using the system and method of the present invention.

Examples of implantable medical devices for the present invention include self-expandable stents, balloon-expandable stents, stent-grafts, sheaths and grafts (e.g., aortic grafts). The underlying structure of the device can be of virtually any design. The device can be made of a metallic material or an alloy such as, but not limited to, cobalt chromium alloy, stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. The device can also be made partially or completely from bioabsorbable or biostable polymers.

System and Method for Coating an Implantable Medical Device

A coating system can be used to coat a stent by loading an applicator with a coating composition and transferring the coating composition from the applicator onto a stent. The coating composition can be applied directly to the surface of the stent, or to a previously applied layer of a coating material. In one embodiment, referring to FIG. 5, a coating system 20 for coating a stent 22 is illustrated to include a composition feeder 24 and an applicator 26. Feeder 24 is used to deposit a coating composition 28 onto applicator 26 adjacent to a lip 30 that holds the deposited coating composition, essentially creating a reservoir at one end of applicator 26. Coating composition 28 can include a solvent and a polymer dissolved in the solvent. Coating composition 28 can optionally include an active agent.

Figure 6:
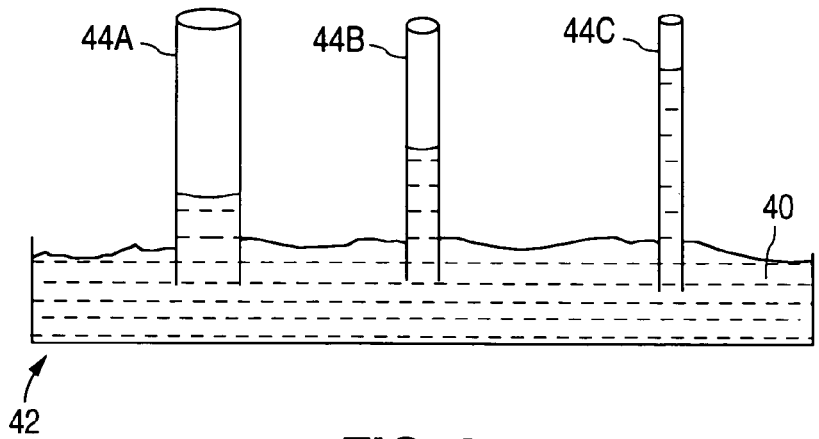
FIG. 6 is an illustration of capillary tubes partially filled by a liquid as a result of capillary action.

Applicator 26 has a porous region 32 that extends through a portion of the body of applicator 26. Porous region 32 is capable of conveying coating composition 28 by capillary action from lip 30 along the length of applicator 26. Capillary action (also known as "wicking") is the force resultant of adhesion, cohesion, and surface tension in liquids which are in contact with solids. For example, referring to FIG. 6, capillary action is the force which causes liquid 40 to be transported upward from a reservoir 42 into vertically oriented capillary tubes 44A, 44B, and 44C. Liquid 40 will rise to a stationary level, $Z\infty$, which is established by the balance between capillary action and gravitational force. $Z\infty$ can be determined by the following equation:

$$Z\infty = \frac{2\gamma\cos\theta}{\rho g r} \quad (1)$$

where γ is the surface tension; θ is wetting angle of liquid 40; ρ is the density of liquid 40; g is the gravitational force; and r is the capillary radius. The flow through capillary tubes 44A, 44B and 44C, dh/dt, can be determined by the following equation:

$$\frac{dh}{dt} = \frac{\gamma r \cos\theta}{4\eta h} - \frac{r^2 \rho g}{8\eta} \quad (2)$$

where γ is the surface tension; r is the capillary radius; θ is wetting angle of liquid 40; η is the viscosity of liquid 40; h is the height of liquid rise; ρ is the density of liquid 40; and g is the gravitational force.

As noted above, the body of applicator 26 includes porous region 32 to receive the coating composition. Porous region 32 is configured so that capillary action through the region can load a layer 34 of coating composition 28 on a coating surface 36 of applicator 26. Representative examples of the thickness of layer 34 include about 2.5 microns to about 1000 microns. In one embodiment, the thickness is about 25 microns to about 100 microns.

Figure 5:
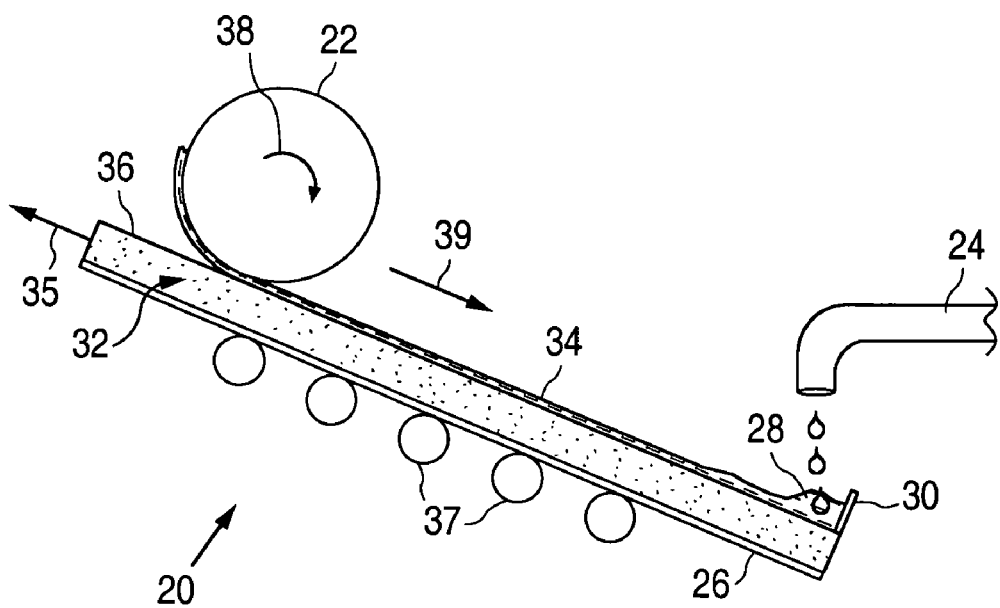
FIG. 5 illustrates a coating system for coating a stent in accordance with one embodiment of the present invention.
Figure 2:
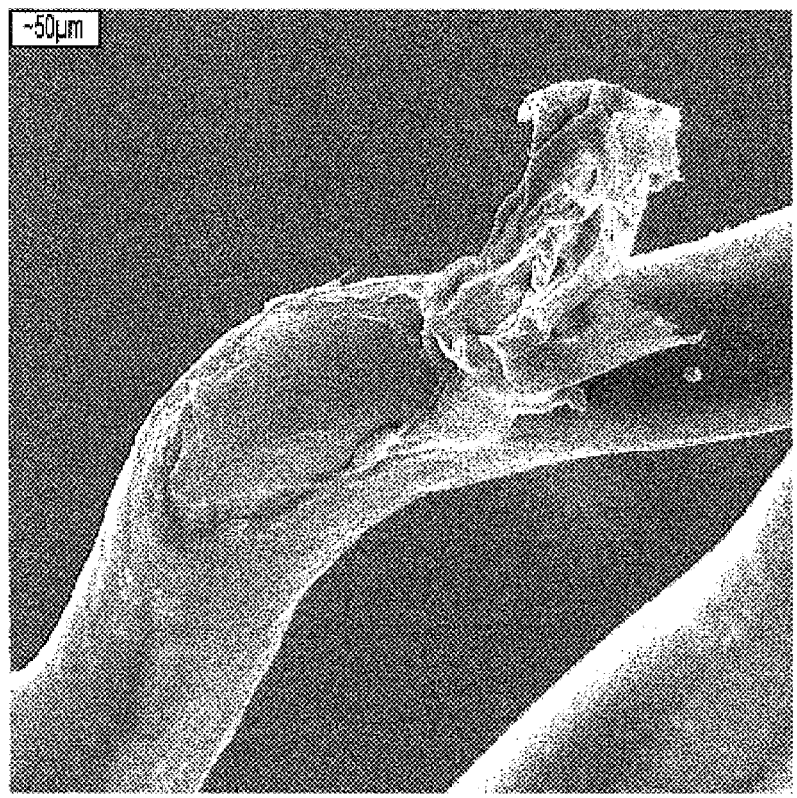
FIGS. 2, 3, and 4 are scanning electron microscope images of stent coatings with coating defects.
Figure 3:
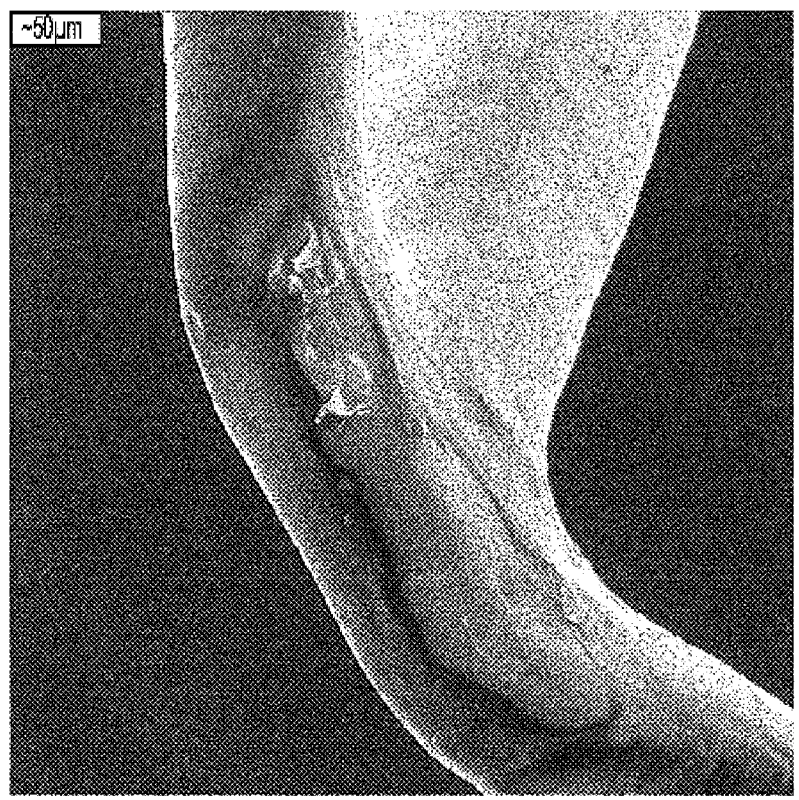
Figure 4:
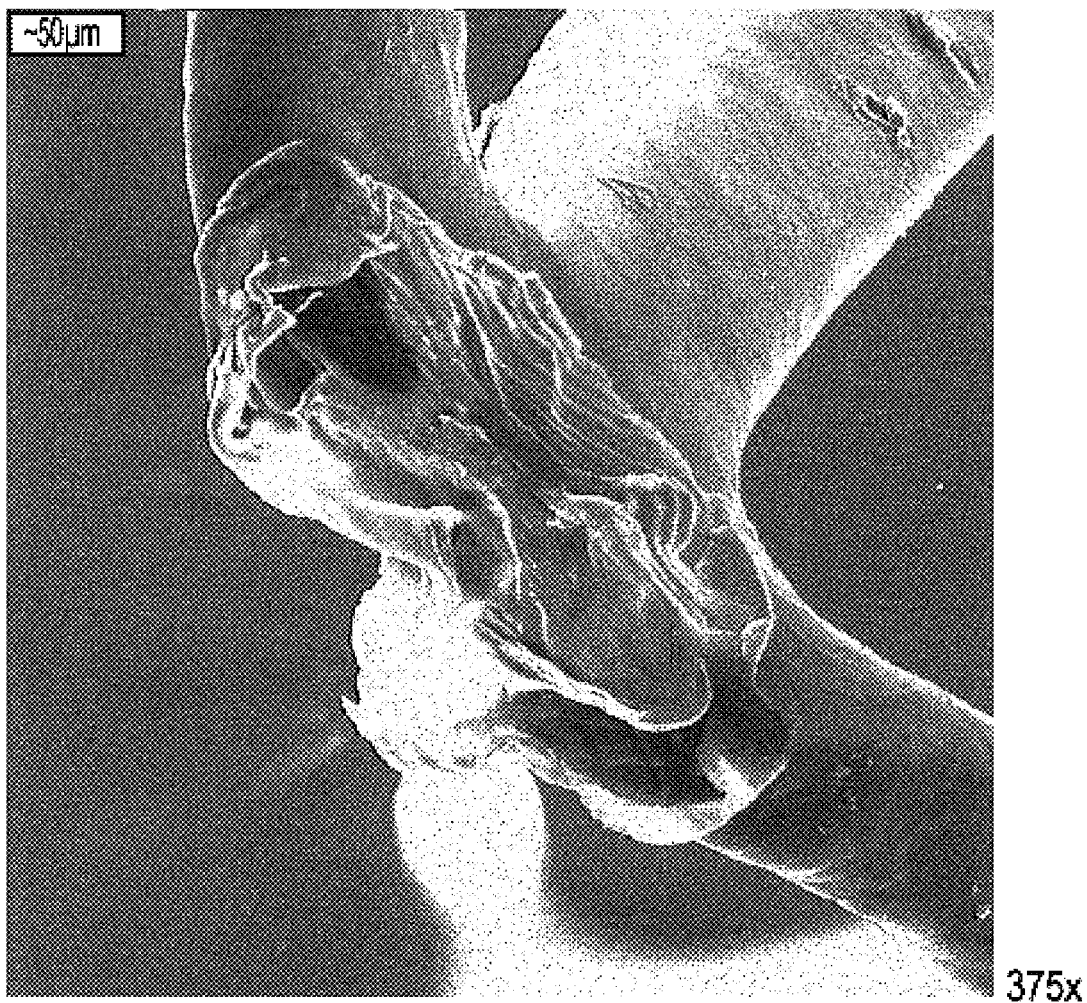

Once layer 34 is formed, stent 22 is rotated in a stationary position (i.e., rotated with no axial movement of stent 22 along applicator 26) or rolled along layer 34 (i.e., both rotational and axial movement of stent 22 along applicator 26) to transfer at least some of coating composition 28 to the outer surface of stent 22 or a coating pre-applied on stent 22. As shown in FIG. 5, the rotational motion of stent 22 is depicted by arrow 38. Rotational speed of stent 22 can be, for example, from about 1 rpm to about 50 rpm, more narrowly from about 1 rpm to about 20 rpm. In one embodiment, stent 22 is supported by a mandrel which is connected to a motor that provides rotational motion to stent 22 during the coating process.

In one embodiment, a portion of layer 34 is transferred to stent 22 while stent 22 is in a substantially horizontal position; in other words, while a longitudinal axis of stent 22 is parallel to or in the plane of the horizon. Coating stent 22 while in a horizontal position can be contrasted with a standard technique of dip coating a vertically positioned stent. When a stent is dip coated while in a vertical position, gravity causes some of the coating to gather at the lower portions of the stent, resulting in an uneven coating along the length of the stent. Coating a stent while in the horizontal position using the systems and methods of the present invention, on the other hand, can produce a more uniform coating along the length of the stent because gravity does not have as much influence on the coating composition after it is applied to the stent.

Figure 7C:
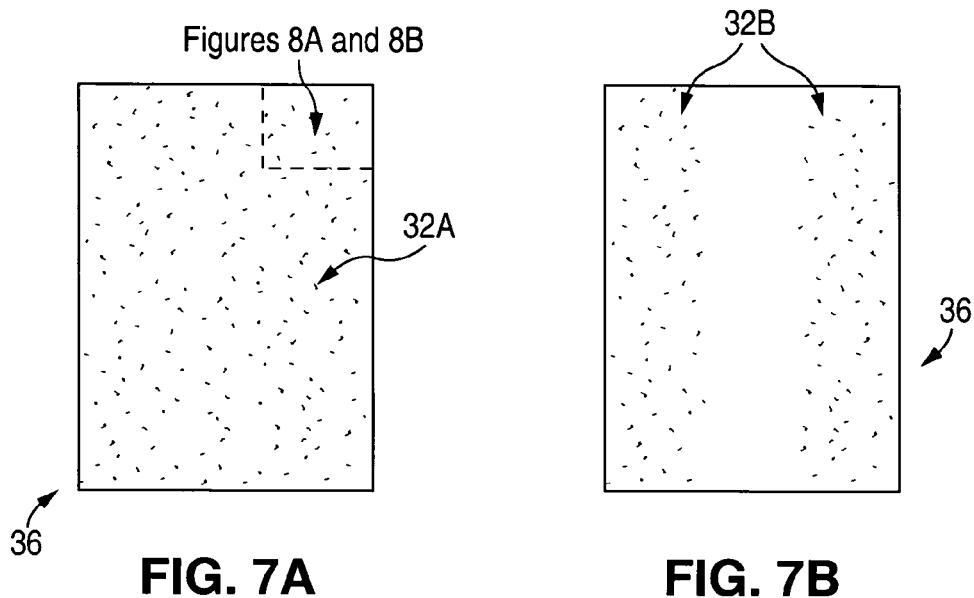
Figure 7C:
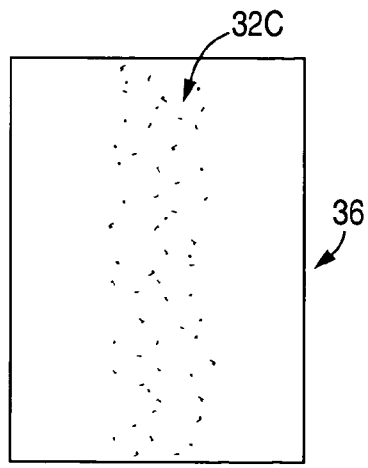

Porous region 32 of applicator 26 is an open pore system (i.e., a network of interconnected pores). Porous region 32 can have any suitable pattern on coating surface 36. Referring to FIG. 7A, which is a top view of coating surface 36, coating surface 36 can have a porous region 32A evenly distributed across the entire surface. Alternatively, referring to FIG. 7B, coating surface 36 can have a porous region 32B only disposed adjacent to the edges of coating surface 36. Coating surface 36 can also have a porous region 32C disposed only in the middle section of coating surface 36 (FIG. 7C). The patterns of porous regions 32B and 32C in FIGS. 7B and 7C, respectively, can be used to selectively apply a coating composition along the body of a stent. For example, if stent 22 is long enough to extend across substantially all of the width of coating surface 36 so that the ends of stent 22 are positioned across a portion of porous region 32B, then the pattern of porous region 32B of FIG. 7B will selectively apply the coating to the end regions of the stent as opposed to the middle segment. The pattern of porous region 32C of FIG. 7C, on the other hand, can be used to selectively coat the middle segment of stent 22.

Figure 8A:
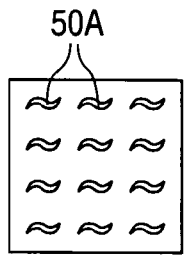
FIGS. 8A and 8B are illustrations of a region of a coating surface in accordance with different embodiments.
Figure 8B:
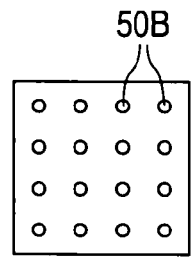

Porous region 32 of applicator 26 can include pores having any suitable shape so that porous region 32 is capable of loading coating composition 28 by capillary action. In one embodiment, pores 50A can have irregular shapes, as illustrated by FIG. 8A. In another embodiment, referring to FIG. 8B, pores 50B of porous region 32 all have a uniform shape such as spherical or cylindrical shape (i.e., circular in a cross section). One advantage of using a porous substrate having pores with a uniform shape is that the porous substrate can act as a filter for the coating composition. For example, the porous substrate can filter out impurities that have particle sizes that are larger than the pores of the porous substrate. Also, if the coating composition includes drug particles, a porous region with uniform pores can trap and filter out those particles that are larger than the pore size.

Porous region 32 of applicator 26 can include pores having any suitable size and have any suitable porosity so that porous region is capable of transporting the coating composition by capillary action. In one embodiment, porous region 32 includes pores having an average pore radius of about 0.1 microns to about 1000 microns, more narrowly, about 0.25 microns to about 90 microns. In another embodiment, porous region 32 has a porosity of about 20% to about 60%, more narrowly, about 40% to about 45%. Porosity is the total volume of pores in the porous region divided by the total volume of the substrate in the porous region. The average pore radius and porosity can be provided by the manufacturer of the selected material, or alternatively can be determined by standard techniques such as mercury penetration porosimetry, or other techniques as described in Gregg et al., Adsorption, Surface Area, and Porosity, $2^{nd}$ ed. (Academic, London, 1982).

Applicator 26 can be made of a porous material that is "non-stick," having a low friction coefficient. The material should be resistant to solvents (e.g., organic solvents such as acetone) and heat, which may be directed onto applicator 26 during the coating process. In one embodiment, applicator 26 is made of a rigid material. A rigid material, as opposed to a pliable or malleable material, can advantageously provide a coating surface that can resist the pressure applied by stent 22 during the application process. This resistance allows for a more uniform coating layer to be transferred to stent 22. Representative examples of materials that can be used for applicator 26 include ceramic materials (such as a suitable brand available from Refractron Technologies Corp., Newark, N.Y.), and polymeric materials such as polyethylene (e.g., Tyvek®, available from DuPont, Wilmington, Del.), and polytetrafluoroethylene (PTFE) (e.g., Teflon®, available from DuPont, Wilmington, Del., or International Polymer Engineering, Inc., Tempe, Ariz.). Ceramic is an especially suitable material because ceramic can transport both aqueous and hydrophobic compositions and is highly resistant to heat and organic solvents.

In one embodiment, referring to FIG. 5, coating surface 36 is completely or substantially flat, and without any curvatures along the length or width of coating surface 36. By providing a flat coating surface 36, the thickness of the coating applied to stent 22 can be substantially uniform.

In some embodiments, applicator 26 can be capable of moving in a linear direction towards stent 22 as indicated by arrow 35 to deposit coating composition 28 on stent 22. Applicator 26 can be integrated with a plurality of rollers 37 to provide axial motion. Applicator 26 can be moved at about 1 mm/second to about 30 mm/second, for example about 6 mm/second. In one embodiment, the movement of applicator 26 will cause stent 22 to rotate by frictional force such that a motor for rotating stent 22 is not needed.

Feeder 24 can be any suitable apparatus configured to deposit coating composition 28 onto applicator 26. To realize greater process efficiency, coating composition 28 can be introduced into the process by means of individually metered, continuous mass flow streams through feeder 24. The flow rate of coating composition 28 from feeder 24 can be from about 0.2 mg/second to about 10 mg/second, for example about 5.0 mg/second.

As coating composition 28 is applied to stent 22, coating composition 28 should be in a substantially free-flowing or liquid form. The viscosity of coating composition 28 when applied onto stent 22 can be at about 10 centipoises at ambient temperature and pressure to about 100 centipoises at ambient temperature and pressure. The consistency of the coating composition can affect the capillary action process and how the composition is received by stent 22.

Figure 9:
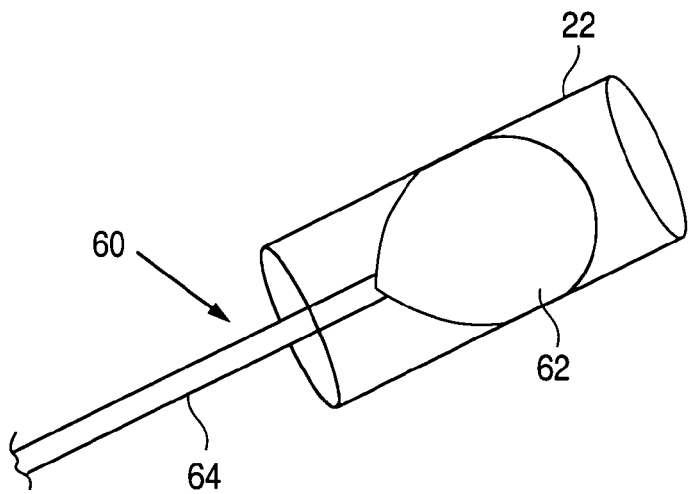
FIG. 9 is a perspective view of a support assembly for a stent to be used during a coating process.

Stent 22 can be supported by a mandrel during the coating process. The mandrel can be used to position stent 22 in close proximity to or in contact with coating surface 36. The mandrel is configured to allow stent 22 to be rotated about a central longitudinal axis of stent 22 during the coating process. The mandrel can also be configured so that stent 22 can be rolled towards lip 30 (i.e., moved in a linear direction as shown by arrow 39). The mandrel can have any design that is suitable to support stent 22 during the coating process. Referring to FIG. 9, stent 22 can be integrated with a mandrel 60 that includes a spring-loaded plug 62 positioned at a distal end of a stem 64. Plug 62 can be circular in cross-section making contact with the inner surface of stent 22. Plug 62 can also have other shapes or designs so long as the intended function of plug 22 is performed. Plug 62 can have an almost equivalent diameter to the inner diameter of stent 22 as positioned on mandrel 60. By way of example, the outer diameter of the plug 62 can be from about 1 mm to about 8 mm.

Plug 62 can be made of materials that are rigid or semi-pliable. In some embodiments, the material can be a "non-stick" material having a low friction coefficient and should be resistant to solvents and heat, which may be directed onto plug 62 during the coating process. Stent 22 can rotate with respect to plug 62 or can be crimped tightly on plug 62 such that the rotation of plug 62 causes stent 22 to rotate. Representative examples of materials that can be used for plug 62 include polyurethanes, polyetheretherketone, polytetrafluoroethylene (e.g., Teflon®), Delrin™, Rulon™, Pebax™, Kynar™, Solef™, fluorinated ethylene-propylene copolymer, poly(vinylidene fluoride-co-chlorotrifluoroethylene), poly(vinyl fluoride), polyesters such as poly(ethylene terephthalate), nylon, stainless steel, titanium alloys, cobalt-chromium alloys, ceramics, metallic carbides, inorganic carbides, and nitrides.

Instead of plug 62, stent 22 can also be held by other support designs. For example, stent 22 can be supported by two plugs, one at each end of stent 22. The two plugs in this type of support apparatus could be connected by an internal mandrel. Alternatively, the two plugs could be unconnected having their relative orientation maintained by an external fixture. The two end plugs can be conical in shape, and therefore, contact stent 22 at contact points at the end struts.

In one embodiment, coating system 20 includes a temperature controller for heating or cooling coating composition 28. The temperature controller can be used to heat or cool coating composition 28 in order to produce and maintain a coating consistency that is suitable for depositing a coating on stent 22. Control over the temperature of coating composition 28 can be especially important for providing adequate conditions for the capillary action of the composition. For instance, the capillary action can be less effective as coating composition 28 becomes more viscous. The temperature controller can include any suitable apparatus for heating or cooling the coating composition, and can be in communication with any suitable component of coating system 20. In one embodiment, applicator 26 is in communication with the temperature controller so that the temperature controller can modify the temperature of coating composition 28 during the coating process. In another embodiment, mandrel 60 is in communication with the temperature controller so that the temperature controller can modify the temperature of stent 22 during the coating process.

Figure 10A:
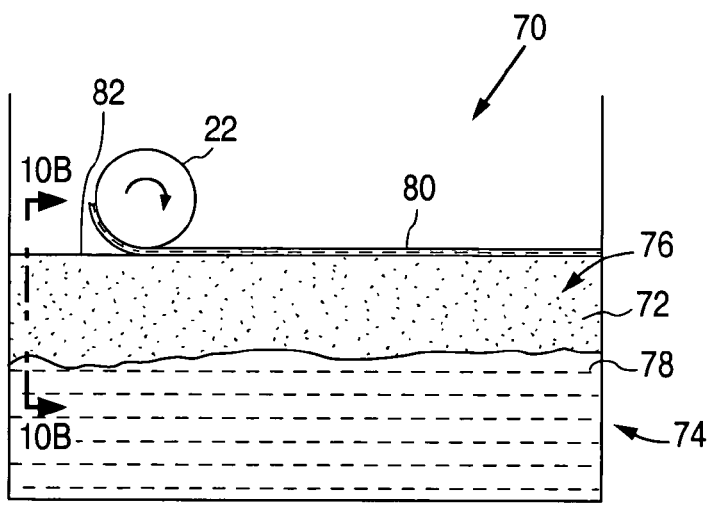
Figure 10B:
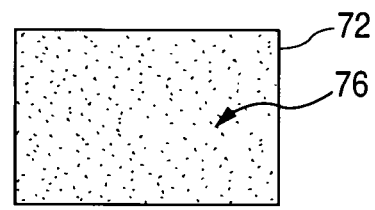

Other embodiments of capillary action applicators will be described hereinafter. In some embodiments, these applicators can have the same property and characteristic as applicator 26. For example, these applicators can have the same porosity and be made from the same materials described above, e.g., ceramics. Referring to FIG. 10A, a coating system 70 including an applicator 72 and a reservoir 74 can be used to apply a layer of a composition to stent 22. Applicator 72 has a porous region 76 that extends at least from the bottom to the top or upper surface of applicator 72. A portion of applicator 72 is partially submerged in a coating composition 78 disposed in reservoir 74 so that at least a portion of porous region 76 of applicator 72 is in contact with coating composition 78. Capillary action through porous region 76 of applicator 72 causes coating composition 78 to be removed from (i.e., wicked from) reservoir 74 and transported through the body of applicator 72 until a layer 80 is formed on a coating surface 82 (i.e., the upper outer surface of applicator 72). Although FIGS. 10A and 10B illustrate an applicator 72 that has porous region 76 that extends through the entire body of applicator 72, porous region 76 can have pores selectively distributed in the body of applicator 72 (e.g., akin to coating surface 36 of FIGS. 7B and 7C) as long as porous region 76 is able to transport coating composition 78 from reservoir 74 to coating surface 82.

A portion of layer 80 can then be transferred to stent 22 by rolling stent 22 along coating surface 82. Stent 22 can be supported by a mandrel and positioned so that stent 22 is in close proximity to or in contact with coating surface 82 as stent 22 is rolled along coating surface 82. A motor can be used to drive stent 22 along coating surface 82.

The viscosity of coating composition 78 in reservoir 74 can be at about 10 centipoises to about 100 centipoises at ambient temperature and pressure. Coating system 70 can include a temperature controller to control the viscosity of coating composition 78. Any suitable component of coating system 70 can be in communication with the temperature controller, such as the mandrel supporting stent 22, applicator 72 and/or reservoir 74.

By positioning applicator 72 in reservoir 74, there can be a continuous loading process. In other words, each time after a portion of coating composition 78 is transferred from coating surface 82 to stent 22, capillary action loads coating surface 82. In one embodiment, applicator 72 is movable within reservoir 74 so that as coating composition 78 is removed from reservoir 74, applicator 72 is lowered into reservoir 74. By allowing applicator 72 to be lowered into reservoir 74 during the coating process, applicator 72 can maintain contact with coating composition 78 disposed in reservoir 74. Applicator 72 can be lowered during the coating process or the rolling of a stent 22. Alternatively, applicator 72 can be lowered between coating applications. Stent 22 can be rotated at least one full cycle followed by lowering of applicator 72. In some embodiments, an amount of composition can be applied to stent 22, followed by drying of the composition or removal of the solvents, followed by lowering of applicator 72 and re-application of the composition. In another embodiment, coating system 70 includes a feeder or pump (not shown) that is configured to deliver coating composition 78 into reservoir 74 as coating composition 78 is transferred onto one or more stents. The feeder or pump can be used to maintain a sufficient level of coating composition 78 within reservoir 74. Reservoir 74 can also include a composition level indicator that is capable of measuring the level of coating composition 78, and indicating when the level is too low. Such a level indicator can be in communication with the feeder or pump in order to automate the process.

The loading of coating surface 82 can be enhanced by application of a pressure. A vacuum apparatus can be used to drawn composition 78 to coating surface 82. For example, FIG. 10A can be a closed chamber such that the top region of the chamber, opposing reservoir 74, is in communication with a vacuum system. Alternatively, reservoir 74 can be pressurized to encourage coating composition 78 to be conveyed from reservoir 74 to coating surface 82. In one embodiment, a gas such as filtered air or an inert gas (e.g., nitrogen) is pumped into reservoir 74 to increase the pressure of reservoir 78.

Figure 11:
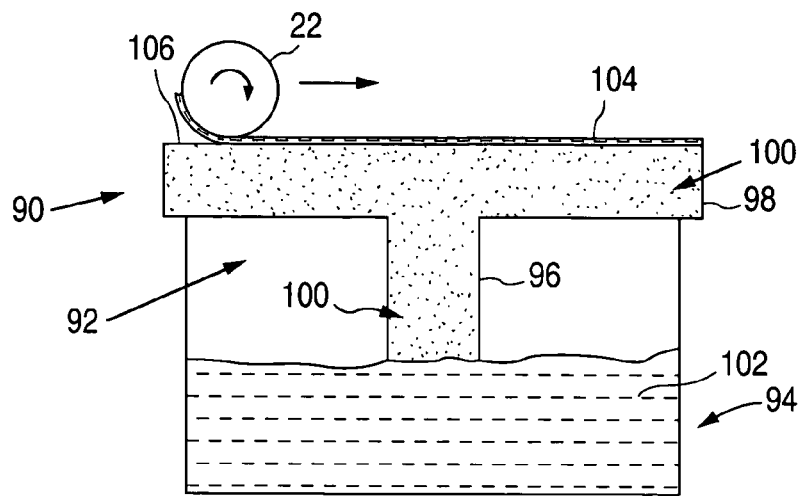

In another embodiment of the present invention, referring to FIG. 11, a coating system 90 including an applicator 92 and a reservoir 94 can be used to apply a layer of composition to stent 22. Applicator 92 includes a first section 96 and a second section 98. Each of the first and second sections 96 and 98 has a porous region 100 disposed along the body of first and second sections 96 and 98 for transporting a coating composition 102 from reservoir 94 to a coating surface 106. First section 96 can act as the primary conveyer of coating composition 102 from reservoir 94. Additionally, first section 96 can be sized or otherwise configured so that first section 96 does not extend across or cover the entire reservoir 94. As best illustrated by FIG. 11, an open space between coating composition 102 and the bottom of second section 96 is therefore provided. By having a first section 96 that does not extend across the entire reservoir 94, less coating composition is necessary to load porous region 100. Also, by configuring applicator 92 to produce an open space, a gas can be more easily delivered to reservoir 94 via the open space, and the increased pressure can be more uniformly delivered to composition 102.

Second section 98, on the other hand, can be sized or otherwise configured so that second section 98 provides a wide platform for coating stents. For example, as shown in FIG. 11, second section 98 can have a length (and width) that is sufficiently longer than reservoir 94 so as to be able to accommodate any number of stents. A sealant can be applied to the area where reservoir 94 and second section 98 contact each other. By sealing this area, if a gas is delivered to reservoir 94, the gas can more effectively increase the pressure of reservoir 94.

The respective porous regions of first and second sections 96 and 98 can have the same or different porosity and average pore radii. In one embodiment, porous regions 100 of first and second sections 96 and 98 have substantially the same porosity, but porous region 100 of first section 96 has pores with a lesser average pore radius than the pores of porous region 100 of second section 98. Smaller pores of first section 96 can convey coating composition 102 from reservoir 94 to a greater height at a faster rate. Then, the larger pores of second section 98 can provide for an ultra-thin layer of coating composition 102 along coating surface 106.

First section 96 of applicator 92 is partially submerged in coating composition 102 disposed in reservoir 94 so that at least a portion of porous region 100 of first section 96 is in contact with coating composition 102. As first section 96 remains partially submerged, capillary action along porous region 100 of first section 96 causes coating composition 102 to be removed from reservoir 94 and into the body of first section 96. After a sufficient loading time, coating composition 102 is transported to second section 98 by capillary action, and ultimately a layer 104 is formed on coating surface 106. Stent 22 can be supported by a mandrel so that stent 22 is in close proximity to or in contact with coating surface 106. Coating composition 102 can then be transferred to stent 22 by rolling stent 22 along coating surface 106 after layer 104 has been loaded with coating composition 102. First and second sections 96 and 98 can be connected in any way that does not interfere with the capillary action process. For example, first and second sections 96 and 98 can be connected with a "tongue and groove" configuration.

Figure 12A:
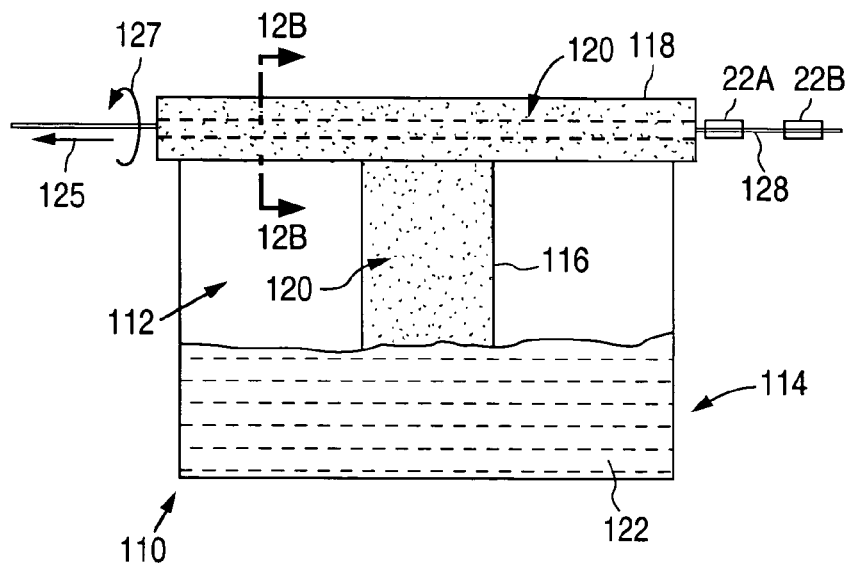
Figure 12B:
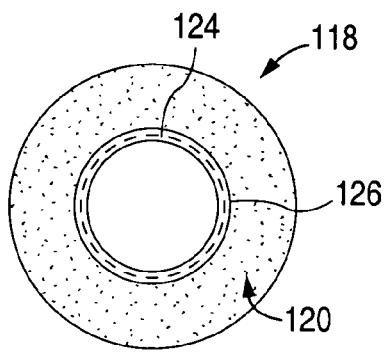

In another embodiment of the present invention, referring to FIGS. 12A and 12B, a coating system 110 including an applicator 112 and a reservoir 114 can be used to apply a layer of a coating composition stent 22. Applicator 112 can include a first section 116 and a second section 118. First and second sections 116 and 118 have a porous region 120 disposed in the body of each section for transporting the composition from reservoir 114 by capillary action. First section 116 of applicator 112 is partially submerged in a coating composition 122 disposed in reservoir 114 so that at least a portion of porous region 120 of first section 116 is in contact with coating composition 122. As first section 116 remains partially submerged, capillary action along porous region 120 of first section 116 causes coating composition 122 to be removed from reservoir 114 and into the body of first section 116. Second section 118 can be configured as a tubular substrate, having a hollow, longitudinal bore. The inner bore of the tube can have a radius of curvature that is about equal to a radius of curvature of stent 22. Coating composition 122 is transferred from reservoir 114 to first section 116, and then to second section 118 by capillary action. A layer 124 of coating composition 122 is then formed on a coating surface 126 (i.e., the inner surface of second section 118).

Coating composition 122 deposited on coating surface 126 can be transferred to stent 22 by inserting stent 22 into the bore of second section 118, and then removing stent 22 from the bore. During insertion and/or removal of stent 22, the outer surface of stent 22 should be in close proximity or in contact with coating surface 126 so that coating composition 122 is transferred to stent 22. Stent 22 can be inserted and removed from the same side of the bore to deposit the coating composition. Alternatively, as shown in FIG. 12A, one or more stents 22A and 22B can be supported by a mandrel 128 that is inserted and taken through the entire length of the bore (e.g., in a linear direction as shown by arrow 125). Stents 22A and 22B can be positioned at a distance from each other as they are taken through the bore in order to give applicator 112 a chance to reload coating surface 126 before the next stent 22 in the series reaches coating surface 126. Furthermore, in order to provide a more uniform coating on stent 22, stent 22 can be rotated while positioned within the bore of second section 118 as shown by arrow 127. In order to transfer the composition from second section 118 to stent 22, the diameter of the bore of second section 118 should be only be slightly greater than the diameter of stent 22. By way of example, the inner diameter of the bore of second section 118 can be from about 0.1 mm to about 0.01 mm larger than the outer diameter of stent 22, for example, 0.01 mm larger. Since stent 22 is radially expandable, when referring to the diameter of stent 22, the measurement is the diameter of stent 22 during the coating process.

As above, a portion of layer 124 can be transferred to stent 22 while stent 22 is in a substantially horizontal position; in other words, while a longitudinal axis of stent 22 is parallel to or in the plane of the horizon. Coating stent 22 while in the horizontal position can produce a uniform coating along the length of stent 22 because gravity does not have as much influence on the coating composition after it is applied to the stent.

Figure 13A:
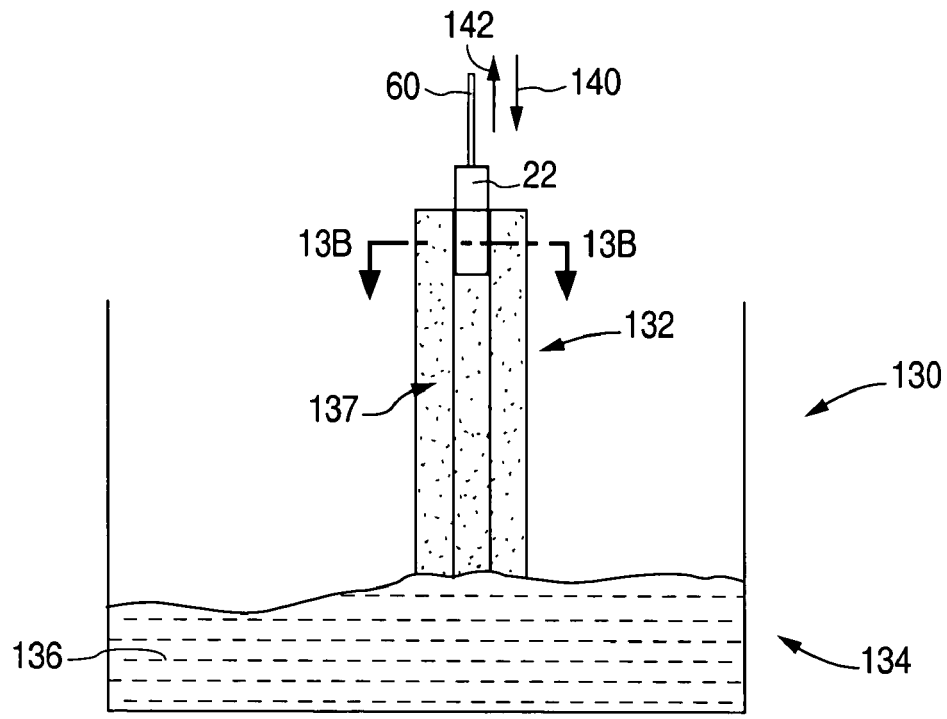
Figure 13B:
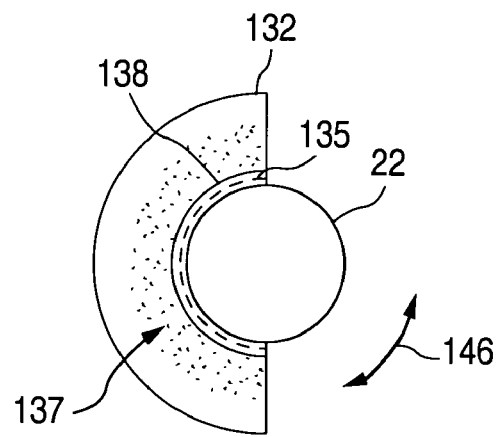

In another embodiment of the present invention, an applicator having a body shaped like a tube or a half-tube can be inserted into a reservoir while in a completely or substantially vertical position in order to load the applicator with a coating composition. Referring to FIGS. 13A and 13B, a coating system 130 can include an applicator 132 and a reservoir 134. Applicator 132 includes a porous region 137 and is configured as a half-tube. Applicator 132 is partially submerged in a coating composition 136 disposed in reservoir 134 so that at least a portion of porous region 137 is in contact with a coating composition 136. As applicator 132 remains partially submerged, capillary action through porous region 137 of applicator 132 causes coating composition 134 to be removed from reservoir 134 into the body of applicator 132, and eventually to deposit a layer 135 of coating composition 136 on coating surface 138.

Coating composition 136 deposited on coating surface 138 can be transferred to stent 22 by inserting stent 22 into the half-bore of applicator 132, and then removing stent 22 up and down as shown by arrows 140 and 142. Stent 22 can be supported by mandrel 60 during the insertion and removal. Stent 22 can be inserted up to any suitable distance into the half-bore. To enhance coating uniformity, stent 22 can be rotated while in the half-bore as shown by arrow 146.

As with other embodiments of the present invention, applicator 132 can be positioned in a horizontal orientation so that a portion of layer 135 can be transferred to stent 22 while stent 22 is in a substantially horizontal position. For example, applicator 132 can replace second section 118 of applicator 112 of FIG. 12A. In such a configuration, coating surface 138 of applicator 132 could be oriented to face away from reservoir 134.

In another embodiment of the present invention, referring to FIGS. 14A-14D, a coating system 150 includes an applicator 152 and a reservoir 154. Coating system 150 can be used to apply a layer of composition to the outer surface of stent 22. Applicator 152 includes a tubular shell 156 that houses a plurality of absorbent fibers 158. Tubular shell 156 is pliable and can be compressed by applying sufficient radial force as shown by arrows 160. Tubular shell 156 can be made of any suitable material that is pliable, such as but not limited to elastic polymeric materials such as rubber, or plastic foam such as polyethylene foam.

Figure 14C:
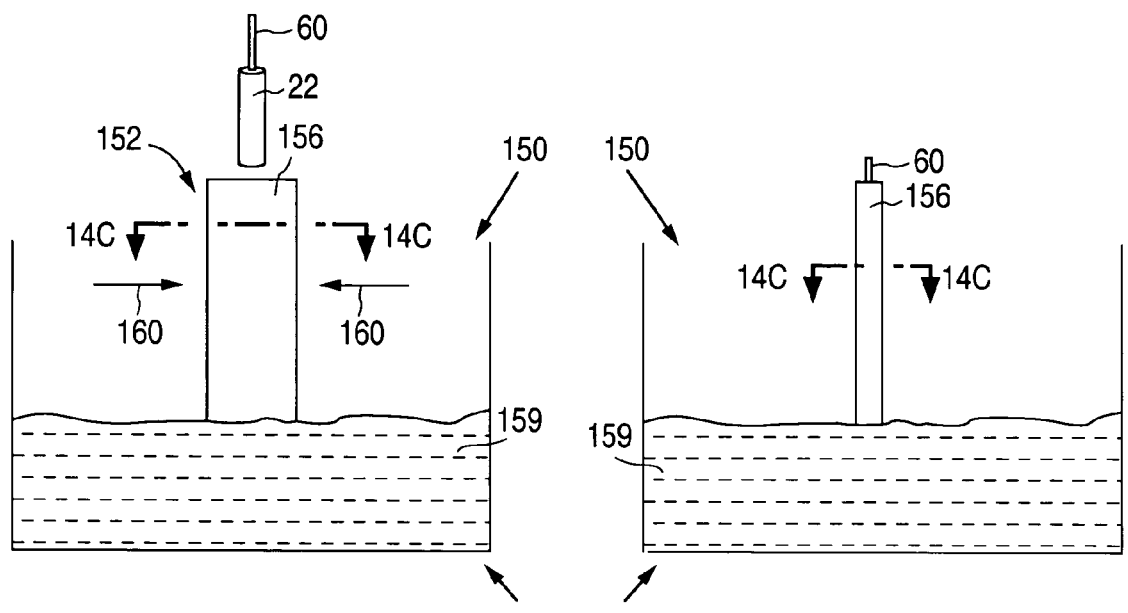
Figure 14C:
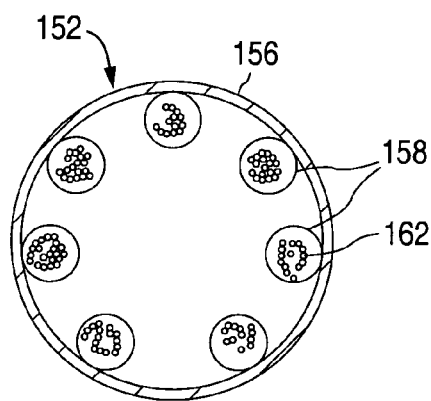
Figure 14D:
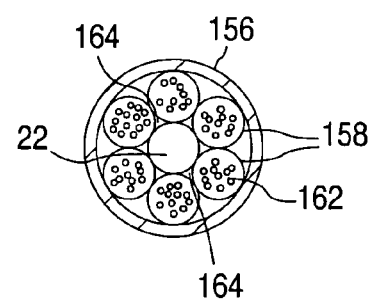

Fibers 158 can have any suitable configuration that allows fibers 158 to transport a coating composition by capillary action and transfer the coating composition to stent 22. Fibers 158 can be configured to have one absorbent filament, or, as shown in FIGS. 14C and 14D, fibers 158 can be configured to include a network of filaments or capillaries 162. If fiber 158 has multiple filaments, the total flow through each fiber is given by the sum of individual flows of each capillary 162 in each fiber. Capillaries 162 can be distributed along the length of fibers 158 in a parallel fashion, or can be woven or braided with each other.

Fibers 158 can be formed of any suitable material that is able to transport a coating composition by capillary action, and otherwise function as disclosed herein. The material used to make fibers 158 should be sufficiently elastic so that fibers 158 do not fracture or otherwise fail when tubular shell 156 is collapsed or compressed as further described below. Furthermore, the material selected for fibers 158 should be compatible with the components of the coating composition, such as the solvent used in the coating composition. Examples of materials that can be used to construct fibers 158 include those materials disclosed in U.S. Pat. No. 5,972,505, among others. Representative examples of materials include carbon; cotton; polyolefins such as polypropylene and polyethylene; polyesters such as poly(ethylene terephthalate); nylon, such as nylon 66 or nylon 6; cellulose esters such as cellulose triacetate or cellulose diacetate; binary blends of cellulose esters with aliphatic polyesters or aliphatic-aromatic copolyesters as well as ternary blends of cellulose esters with aliphatic polyester/polyacrylates, aliphatic polyesters/polyvinyl acetates/aliphatic polyesters/polyvinyl alcohol, aliphatic polyesters/polyvinyl chloride, aliphatic polyesters/polycarbonate, aliphatic polyesters/polyvinyl acetate-polyethylene copolymer, aliphatic polyesters/cellulose ethers, aliphatic polyesters/nylon, aliphatic-aromatic copolyesters/polyacrylates/aliphatic-aromatic copolyesters/polyvinyl acetates, aliphatic-aromatic copolyesters/polyvinyl alcohol, aliphatic-aromatic copolyesters/polyvinyl chloride, aliphatic-aromatic copolyesters/polycarbonate, aliphatic-aromatic copolyesters/polyvinyl acetate-polyethylene copolymer, or aliphatic-aromatic copolyesters/cellulose ethers, and aliphatic-aromatic copolyesters/nylon.

Fibers 158 can be formed by any suitable method. For example, by the methods described in U.S. Pat. No. 5,972,505 and Neimark et al., Hierarchical Pore Structure and Wetting Properties of Single-Wall Carbon Nanotube Fibers, Nano Letters, 3(3):419-23 (2003).

In operating coating system 150, fibers 158 can be partially submerged in a coating composition disposed in reservoir 154. As fibers 158 remain partially submerged, capillary action along the length of fibers 158 causes the coating composition to be removed from reservoir 154 into fibers 158. Coating composition 159 can be transferred to stent 22 by inserting stent 22 into tubular shell 156 and compressing tubular shell 156 so that fibers 158 transfer coating composition 159 to the outer surface of stent 22. Stent 22 can be inserted up to any suitable distance into tubular shell 156. If stent 22 is to be coated along the entire length of stent 22, stent 22 should be completely inserted into tubular shell 156. After stent 22 has been inserted at the selected distance, tubular shell 156 should be compressed to a sufficient radius so that fibers 158 are in close proximity or in contact with the outer surface of stent 22. To enhance coating uniformity, fibers 158 can be sized and/or positioned so that there are few or no gaps 164 between fibers 158 and the stent surface. Additionally, stent 22 can be rotated while fibers 158 are compressed against the stent surface to enhance coating uniformity.

In another embodiment, a system is provided for coating an inner surface of stent 22. Coating just the inner surface can be advantageous for the delivery of therapeutic agents to the blood system to prevent thrombosis or promote rapid reendothelialization. For instance, certain drugs may effectively treat cardiovascular injuries when carried away by the blood flow to an area adjacent to the site of stent implantation. These drugs, for example, may be used to treat "edge restenosis."

Figure 15A:
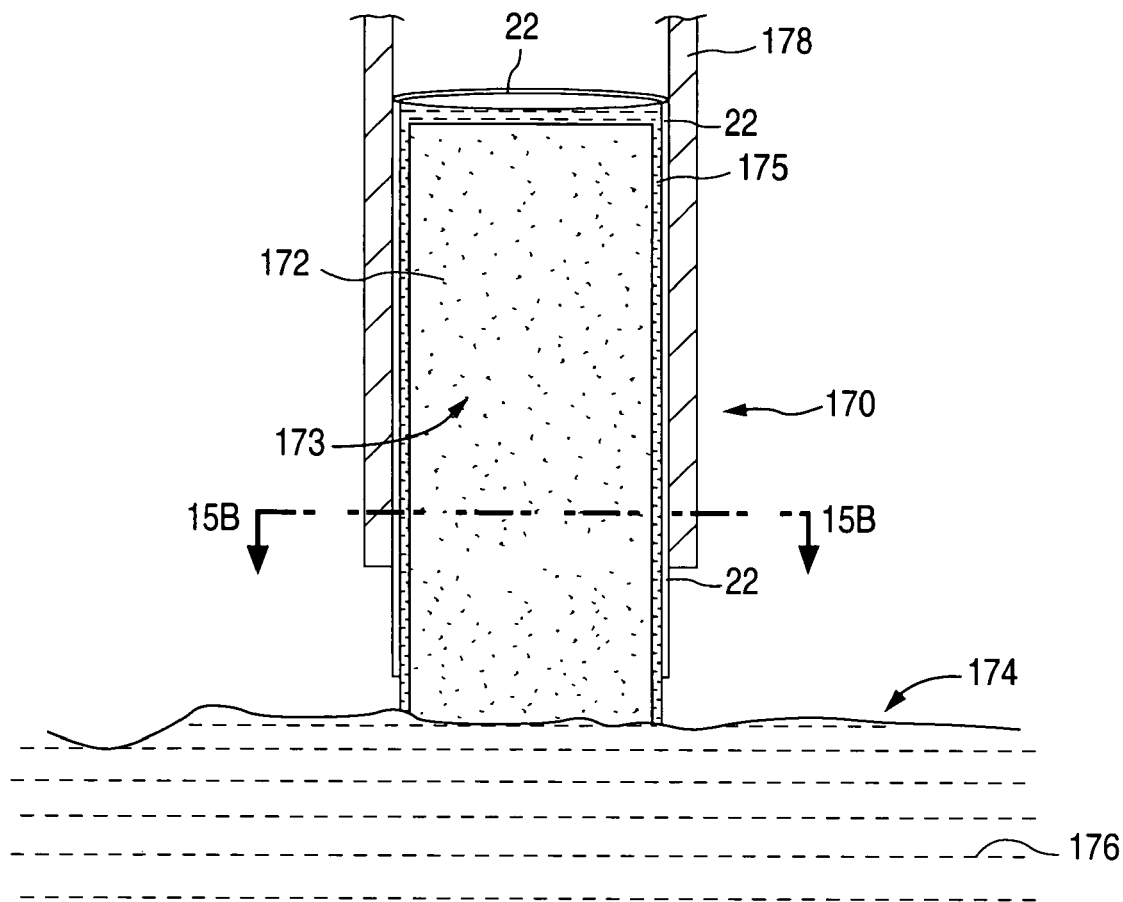
FIGS. 15A, 15B, 16A and 16B illustrate coating systems for coating an inner surface of a stent in accordance with other embodiments of the present invention.
Figure 15B:
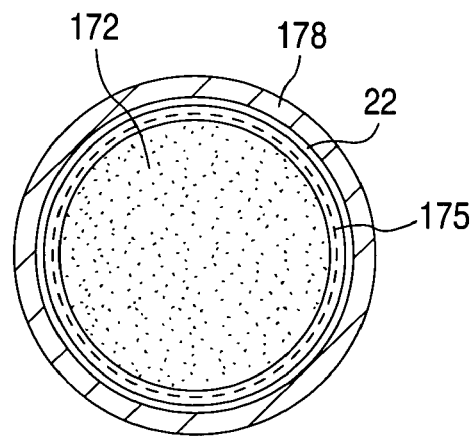

Referring to FIGS. 15A and 15B, a coating system 170 can include an applicator 172 and a reservoir 174. Applicator 172 includes a porous region 173 and has a cylindrical shape. Applicator 172 has porous region 173 disposed in the body of applicator 172 for transporting the composition from reservoir 174. Applicator 172 is partially submerged in a coating composition 176 disposed in reservoir 174 so that at least a portion of porous region 173 is in contact with coating composition 176. As applicator 172 remains partially submerged, capillary action through porous region 173 of applicator 172 causes coating composition 176 to be removed from reservoir 174 into the body of applicator 172, and eventually to form a layer 175 on the outer surface of applicator 172.

Stent 22, in turn, can be supported in a tube 178. Tube 178 should have an inner diameter that allows tube 178 to grip and mask a portion of the outer diameter of stent 22. Applicator 172 can be sized to provide an effective circumference to deliver a coating composition to the inner surface of stent 22. By way of example, the outer diameter of applicator 172 can be about 0.1 mm to about 0.01 mm, for example, 0.01 mm less than the inner diameter of stent 22. In one embodiment, applicator 172 and/or tube 178 are in communication with a temperature controller.

Figure 16A:
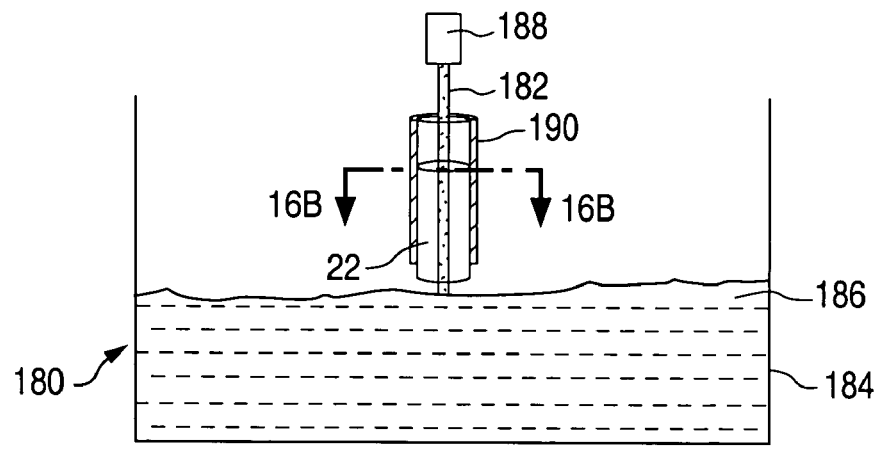
Figure 16B:
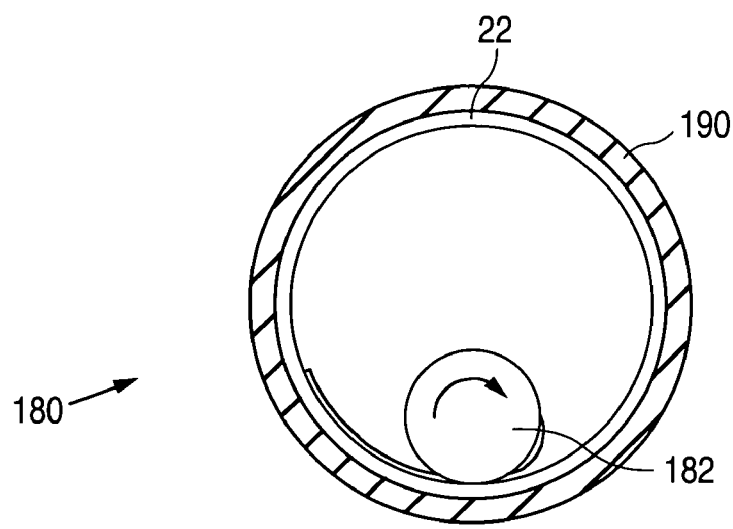

Referring to FIGS. 16A and 16B, a coating system 180 is provided for coating the inner surface of a stent 22 including an applicator 182 and a reservoir 184 for holding a coating composition 186. Applicator 182 includes a porous region disposed through the body of applicator 182. Applicator 182 is integrated with a grip 188 that is substantially free from pores so that applicator 182 can be handled without contacting wet composition. Stent 22, in turn, can be supported in a tube 190. The outer surface of applicator 182 can be coated with a wet coating by capillary action before contacting the inner surface of stent 22. Applicator 182 can then be rolled around the inner circumference of stent 22. As with the above described embodiments, coating system 180 can include a temperature controller for heating or cooling coating composition 186 during the coating process.

Multiple repetitions for applying the coating composition can be performed using the system and method of the present invention. As noted above, selective components of the coating systems as described herein can be disposed in a pressure chamber so that the pressure can be altered at any time during the coating process. The amount of composition applied by each repetition can be about 1 microgram/cm$^2$ (of stent surface) to about 100 milligrams/cm$^2$, for example about 100 micrograms/cm$^2$ per application. Each repetition can be followed by removal of a significant amount of the solvent(s). Depending on the volatility of the particular solvent employed, the solvent can evaporate essentially upon contact with the stent. Alternatively, removal of the solvent can be induced by baking the stent in an oven at a mild temperature (e.g., 60° C.) for a suitable duration of time (e.g., 2-4 hours) or by the application of warm air. The application of warm air between each repetition-prevents coating defects and minimizes interaction between the active agent and the solvent. The temperature of the warm air can be from about 30° C. to about 60° C., more narrowly from about 40° C. to about 50° C. The flow rate of the warm air can be from about 20 cubic feet/minute (CFM) (0.57 cubic meters/minute (CMM)) to about 80 CFM (2.27 CMM), more narrowly about 30 CFM (0.85 CMM) to about 40 CFM (1.13 CMM). The warm air can be applied for about 3 seconds to about 60 seconds, more narrowly for about 10 seconds to about 20 seconds. By way of example, warm air applications can be performed at a temperature of about 50° C., at a flow rate of about 40 CFM, and for about 10 seconds.

Any suitable number of repetitions of applying the composition followed by removing the solvent(s) can be performed to form a coating of a desired thickness or weight. The coating process as described herein can be used to form a coating on the stent having a thickness of about 0.1 microns to about 100 microns, more narrowly, about 0.5 micron to about 20 microns.

Operations such as wiping, centrifugation, or other web clearing acts can also be performed to achieve a more uniform coating. Briefly, wiping refers to the physical removal of excess coating from the surface of the stent; and centrifugation refers to rapid rotation of the stent about an axis of rotation. The excess coating can also be vacuumed off of the surface of the stent.

The stent can be at least partially preexpanded prior to the application of the composition. For example, the stent can be radially expanded about 20% to about 60%, more narrowly about 27% to about 55%—the measurement being taken from the stent's inner diameter at an expanded position as compared to the inner diameter at the unexpanded position. The expansion of the stent, for increasing the interspace between the stent struts during the application of the composition, can further prevent "cob web" formation between the stent struts.

Coating Composition

As noted above, the coating composition can include a solvent and a polymer dissolved in the solvent, and optionally an active agent. Representative examples of polymers that can be used to coat a medical device in accordance with the present invention include ethylene vinyl alcohol copolymer (commonly known by the generic name EVOH or by the trade name EVAL); poly(hydroxyvalerate); poly(lactic acid) including poly(L-lactic acid), poly(D-lactic acid) and poly(D,L-lactic acid), and copolymers thereof such as poly(lactide-co-glycolide); polycaprolactone; poly(hydroxybutyrate); poly(hydroxybutyrate-co-valerate); polydioxanone; polyorthoester; polyanhydride; poly(glycolic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether-esters) (e.g., PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride, polyvinylidene chloride poly(vinylidene fluoride-co-hexafluoropropene), and poly(vinylidene fluoride-co-chlorotrifluoroethylene); polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

"Solvent" is defined as a liquid substance or composition that is compatible with the polymer and is capable of dissolving the polymer at the concentration desired in the composition. Examples of solvents include, but are not limited to, dimethylsulfoxide, chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methyl pyrrolidinone, toluene, and combinations thereof.

The active agent can be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect for the subject. For example, the agent can be for enhancing wound healing in a vascular site or improving the structural and elastic properties of the vascular site.

By using the system and method of the present invention, the same active agent can be applied to the inner and outer surfaces of stent 22. Alternatively, different active agents can be applied to the two surfaces. For example, the outer surface of stent 22 can be coated with a drug that is capable of treating restenosis. The inner surface of stent 22, on the other hand, can be coated with an angiogenic drug.

Examples of agents include antiproliferative substances such as actinomycin D, or derivatives and analogs thereof (manufactured by Sigma-Aldrich 1001 West Saint Paul Avenue, Milwaukee, Wis. 53233; or Cosmegen available from Merck). Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g., Taxol® by Bristol-Myers Squibb Co., Stamford, Conn.), docetaxel (e.g., Taxotere®, from Aventis S.A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is pemirolast potassium. Other therapeutic substances or agents which may be appropriate include alpha-interferon, genetically engineered epithelial cells, dexamethasone and rapamycin and structural derivatives or functional analogs thereof, such as 40-O-(2-hydroxy)ethyl-rapamycin (known as everolimus, available from Novartis), 40-O-(3-hydroxy)propyl-rapamycin, 40-O-[2-(2-hydroxy)ethoxy]ethyl-rapamycin, and 40-O-tetrazole-rapamycin.

EXAMPLES

Some embodiments of the present invention are illustrated by the following Examples. The Examples are being given by way of illustration only and not by way of limitation. The parameters and data are not be construed to unduly limit the scope of the embodiments of the invention.

Example 1

A 18 mm Vision stent (available from Guidant Corporation) was placed over a solid mandrel to fully support the stent along the length of the stent. A coating composition was prepared. The coating composition included 3% (w/w) poly (lactic acid) and 97% acetone (w/w). The coating composition was transferred to a stainless steel cell to be used as a reservoir. A two inch diameter porous ceramic disk with an average pore radius of 6 μm (available from Refractron Technologies Corp., Newark, N.Y.) was partially submerged in the coating composition held by the reservoir. A thin, wet film of the coating composition was quickly formed on the upper surface of the disk. The mounted stent was rolled over the upper surface of the ceramic disk by hand at one revolution per second to transfer a portion of the film to the outer surface of the stent. The stent was weighed after the application, and it was determined that about 25 μg to about 30 μg of coating composition had been applied to the stent.

Example 2

A 18 mm Vision stent (available from Guidant Corporation) was placed over a solid mandrel to fully support the stent along the length of the stent. The coating composition of Example 1 was transferred to a stainless steel cell to be used as a reservoir. A two inch porous ceramic disk with an average pore radius of 6 μm (available from Refractron Technologies Corp., Newark, N.Y.) was partially submerged in the coating composition held by the reservoir. A thin, wet film of the coating composition was quickly formed on the upper surface of the disk. The mounted stent was rolled over the upper surface of the ceramic disk by hand to transfer a portion of the film to the outer surface of the stent. The rolling process was repeated for three additional times. The stent was weighed after the application, and it was determined that about 75 μg of coating composition had been applied to the stent.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A system for coating an implantable medical device with a coating composition, comprising:

a reservoir holding a coating composition;

an applicator including a coating surface and a porous region in fluid communication with the coating composition in the reservoir, wherein the porous region is capable of conveying the coating composition from the reservoir to the coating surface, the applicator further including:
   a first section having a porous region disposed in the coating composition in the reservoir, and
   a second section having a porous region in fluid communication with the porous region of the first section, the second section being disposed over the first section so as to provide a sealed space between the second section and the coating composition in the reservoir, wherein the second section includes the coating surface to coat the implantable medical device;
a support element to support an implantable medical device in close proximity to or in contact with the coating surface of the applicator;
a temperature controller in communication with the applicator, the support element or the reservoir for heating or cooling the coating composition; and
a pressurizing device in communication with the applicator or the reservoir for enhancing the conveyance of the coating composition from the reservoir to the coating surface wherein the pressurizing device is in fluid communication with the sealed space.

2. The system of claim 1, wherein the applicator comprises a hollow tubular body having a bore, the bore being configured to received the device.

3. The system of claim 1, wherein the applicator comprises a half-tubular body configured to receive the device.

4. The system of claim 1, wherein the coating surface comprises a completely or substantially flat substrate on which the device can be placed.

5. The system of claim 1, wherein the at least one of the porous regions comprises pores having an average pore radius of about 0.1 microns to about 1000 microns.

6. The system of claim 1, wherein at least one of the porous regions has a porosity of about 20% to about 60%.

7. The system of claim 1, additionally including an apparatus to rotate the support element.

8. The system of claim 1, wherein the applicator is movable in a linear direction.

9. The system of claim 1, wherein the device is a stent.

10. The system of claim 1, wherein the applicator is made from a ceramic or polymeric material.

11. The system of claim 1, wherein the applicator is made from a rigid material such that the coating surface does not comply when the device contacts the coating surface.

12. The system of claim 1, wherein the second section of the applicator comprises a hollow tubular body having a longitudinal bore configured to receive the implantable medical device.

13. The system of claim 1, wherein the porous region of the first section has an average pore size smaller than the average pore size of the porous region of the second section.

14. The system of claim 1, wherein the applicator has a uniform pore pattern.

15. The system of claim 1, wherein the applicator includes a network of interconnected pores.

16. The system of claim 1, wherein the applicator includes pores that are sized such that particles within the coating composition that exceed a predetermined size are not capable of being conveyed to the coating surface.

17. A system for coating an implantable medical device with a coating composition, comprising:
   a reservoir of coating composition;
   an applicator in fluid communication with the reservoir, the applicator including a porous coating portion having a coating surface, and a porous portion for conveying coating composition from the reservoir to the coating portion, wherein a length and/or width of the coating portion is substantially greater than a length and/or width of the porous portion; and
   a support element to support an implantable medical device in close proximity to or in contact with the coating surface of the applicator;
   wherein the reservoir has walls and the walls, the porous portion and the coating portion form a closed space containing at least a portion of the coating composition contained in the reservoir, further including:
      a pressure device in fluid communication with the space and configured for regulating the coating composition conveyed to the coating surface by regulating the pressure in the space.

18. The system of claim 17, wherein the coating surface is horizontally disposed above the reservoir.

19. The system of claim 17, wherein a portion of the applicator is partially submerged in the reservoir.

20. The system of claim 17, wherein a surface of the coating portion facing the coating composition contained in the space is sealed.

21. The system of claim 17, wherein the coating portion includes a coating surface formed by a horizontally disposed cylinder.

22. The system of claim 17, wherein the coating portion has a first average pore size and the porous portion has a second average pore size that is smaller than the first average pore size.

23. A system for coating an implantable medical device with a coating composition, comprising:
   a reservoir holding a coating composition;
   an applicator including a coating surface and a porous region in fluid communication with the coating composition in the reservoir, wherein the porous region is capable of conveying the coating composition from the reservoir to the coating surface;
   a support element to support an implantable medical device in close proximity to or in contact with the coating surface of the applicator; and
   a pressure apparatus configured to supply a gas to, and being in fluid communication with the coating composition so as to enhance the loading of the coating surface.

24. The system of claim 23, further including the reservoir, coating composition and/or applicator forming a closed space and the pressure apparatus draws a vacuum in the closed space.

25. The system of claim 23, wherein the pressure apparatus supplies a gas to the coating composition to enhance the loading of the coating surface.

* * * * *